United States Patent
Von Kleist et al.

(10) Patent No.: US 12,376,748 B2
(45) Date of Patent: Aug. 5, 2025

(54) FETAL CARDIAC MRI USING SELF-GATING WITH A CARTESIAN K-SPACE TRAJECTORY

(71) Applicant: Children's Medical Center Corporation, Boston, MA (US)

(72) Inventors: Henrik Q Von Kleist, Munich (DE); Andrew Powell, Dedham, MA (US); Mehdi Hedjazi Moghari, Auburndale, MA (US)

(73) Assignee: Children's Medical Center Corporation, Boston, MA (US)

(*) Notice: Subject to any disclaimer, the term of this patent is extended or adjusted under 35 U.S.C. 154(b) by 275 days.

(21) Appl. No.: 17/921,473

(22) PCT Filed: Apr. 26, 2021

(86) PCT No.: PCT/US2021/029116
§ 371 (c)(1),
(2) Date: Oct. 26, 2022

(87) PCT Pub. No.: WO2021/222082
PCT Pub. Date: Nov. 4, 2021

(65) Prior Publication Data
US 2023/0181041 A1 Jun. 15, 2023

Related U.S. Application Data

(60) Provisional application No. 63/016,183, filed on Apr. 27, 2020.

(51) Int. Cl.
*A61B 5/00* (2006.01)
*A61B 5/024* (2006.01)
(Continued)

(52) U.S. Cl.
CPC ........ *A61B 5/0044* (2013.01); *A61B 5/02411* (2013.01); *A61B 5/055* (2013.01);
(Continued)

(58) Field of Classification Search
CPC .............................. A61B 5/055; A61B 5/0044
See application file for complete search history.

(56) References Cited

U.S. PATENT DOCUMENTS

2004/0155653 A1  8/2004  Larson et al.
2008/0183092 A1  7/2008  Smith et al.
(Continued)

OTHER PUBLICATIONS

Bastkowski, Rene, et al. "Self-gated golden-angle spiral 4D flow MRI." Magnetic resonance in medicine 80.3 (2018): 904-913.*
(Continued)

*Primary Examiner* — Carolyn A Pehlke
(74) *Attorney, Agent, or Firm* — Greenberg Traurig, LLP; Andrew J. Tibbetts; Samuel S. Stone

(57) ABSTRACT

Fetal cardiac magnetic resonance (MR) images of a living fetus, within a uterus of a parent of the fetus, can be generated by imaging the fetus within the uterus using a magnetic resonance imaging (MRI) system. Information indicative of fetal cardiac cycles can be derived from MR data obtained by an MRI system while imaging the fetus, the MR data including MR data for the center of k-space. The derived information may be used to differentiate the fetal cardiac cycles from other sources of noise in the MR data such as the parental cardiac cycles.

23 Claims, 11 Drawing Sheets

(51) Int. Cl.
  A61B 5/055   (2006.01)
  G01R 33/48   (2006.01)
  G01R 33/563  (2006.01)
  G01R 33/567  (2006.01)
(52) U.S. Cl.
  CPC .......... *A61B 5/7289* (2013.01); *G01R 33/482* (2013.01); *G01R 33/56325* (2013.01); *G01R 33/5673* (2013.01); *A61B 2503/02* (2013.01)

(56) References Cited

U.S. PATENT DOCUMENTS

| | | |
|---|---|---|
| 2015/0374237 A1 | 12/2015 | Hu et al. |
| 2018/0368803 A1 | 12/2018 | Kording et al. |
| 2019/0033411 A1 | 1/2019 | Katscher et al. |

OTHER PUBLICATIONS

Guo, Liheng, J. Andrew Derbyshire, and Daniel A. Herzka. "Pseudo-projection-driven, self-gated cardiac cine imaging using cartesian golden step phase encoding." Magnetic resonance in medicine 76.2 (2016): 417-429.*

Greenberg, Julie. "Blind Source Separation: Principal & Independent Component Analysis." (2007).*

PCT/US2021/029116, Aug. 31, 2021, International Search Report and Written Opinion.

PCT/US2021/029116, Nov. 10, 2022, International Preliminary Report on Patentability.

International Search Report and Written Opinion for International Application No. PCT/US2021/029116 mailed Aug. 31, 2021.

International Preliminary Report on Patentability for International Application No. PCT/US2021/029116 mailed Nov. 10, 2022.

Belouchrani et al., A blind source separation technique using second-order statistics. IEEE Trans Signal Process Feb. 1997;45(2):434-444.

Bhat et al., Fetal iGRASP cine CMR assisting in prenatal diagnosis of complicated cardiac malformation with impact on delivery planning. Clinical Physiology and Functional Imaging. Jul. 2019;39(4):231-5.

Bonanno et al., Self-gated golden angle spiral cine MRI for coronary endothelial function assessment. Magnetic Resonance Medicine. 2018;80(2):560-570.

Brix et al., Overcoming foetal motion using interactive real-time magnetic resonance imaging. Clinical Physiology and Functional Imaging. 2017;37(6):717-22.

Budorick et al., New modalities for imaging the fetal heart. Seminars in Perinatology. Oct. 2000;24(5):352-359.

Buehrer et al., Prospective self-gating for simultaneous compensation of cardiac and respiratory motion. Magnetic resonance in medicine. Sep. 2008;60(3):683-90.

Cardoso, Blind signal separation: statistical principles. Proceedings of the IEEE. Oct. 1998;86(10):2009-25.

Castells et al., Spatiotemporal blind source separation approach to atrial activity estimation in atrial tachyarrhythmias. IEEE transactions on biomedical engineering. Feb. 2005;52(2):258-67.

Coakley et al., Fetal MRI: a developing technique for the developing patient. American Journal of Roentgenology. Jan. 2004;182(1):243-52.

Crowe et al., Automated rectilinear self-gated cardiac cine imaging. Magnetic Resonance in Medicine: An Official Journal of the International Society for Magnetic Resonance in Medicine. Oct. 2004;52(4):782-8.

De Sousa et al., Dynamic fetal cardiac magnetic resonance imaging in four-chamber view using Doppler ultrasound gating in normal fetal heart and in congenital heart disease: comparison with fetal echocardiography. Ultrasound in Obstetrics & Gynecology. May 2019;53(5):669-75.

Deng et al., Current applications of fetal cardiac imaging technology. Current opinion in Obstetrics and Gynecology. 2006;18(2):177-84.

Deng et al., New fetal cardiac imaging techniques. Prenatal Diagnosis: Published in Affiliation With the International Society for Prenatal Diagnosis. Dec. 30, 2004;24(13):1092-103.

Dong et al., Preliminary experience with cardiovascular magnetic resonance in evaluation of fetal cardiovascular anomalies. Journal of Cardiovascular Magnetic Resonance. Dec. 2013; 15(1):1-2.

Eckersley et al., Fetal CINE Cardiac Magnetic Resonance Imaging: The Final Frontier in Fetal Cardiac Imaging ?. Circulation: Cardiovascular Imaging. Dec. 2018;11(12):e008458.

Fessler et al., Nonuniform fast Fourier transforms using min-max interpolation. IEEE transactions on signal processing. Feb. 2003;51(2):560-74.

Finn et al., Cardiac MR imaging: state of the technology. Radiology. Nov. 2006;241(2):338-54.

Fogel et al., Preliminary investigations into a new method of functional assessment of the fetal heart using a novel application of 'real-time'cardiac magnetic resonance imaging. Fetal diagnosis and therapy. 2005;20(5):475-80.

Fuchs et al., TrueFISP—technical considerations and cardiovascular applications. European journal of radiology. Apr. 1, 2003;46(1):28-32.

Gorincour et al., Feasibility of fetal cardiac magnetic resonance imaging: preliminary experience. Ultrasound in obstetrics & gynecology: the official journal of the International Society of Ultrasound in Obstetrics and Gynecology. Jan. 2007;29(1):105-8.

Guo et al., Pseudo-projection-driven, self-gated cardiac cine imaging using cartesian golden step phase encoding. Magnetic resonance in medicine. Aug. 2016;76(2):417-29.

Guo et al., Screening of fetal CNS anomalies by MR imaging. Child's Nervous System. Aug. 2003;19:410-4.

Guo et al., The state of the art of fetal magnetic resonance imaging. Chinese medical journal. Aug. 5, 2006;119(15):1294-9.

Han et al., Prospective cardiac motion self-gating. Quantitative imaging in medicine and surgery. Apr. 2017;7(2):215-226.

Haris et al., Self-gated fetal cardiac MRI with tiny golden angle iGRASP: A feasibility study. Journal of Magnetic Resonance Imaging. Jul. 2017;46(1):207-17.

Hiba et al., Cardiac and respiratory self-gated cine MRI in the mouse: Comparison between radial and rectilinear techniques at 7T. Magnetic Resonance in Medicine: An Official Journal of the International Society for Magnetic Resonance in Medicine. Oct. 2007;58(4):745-53.

Holmes et al., In ovo non-invasive quantification of the myocardial function and mass of chick embryos using magnetic resonance imaging. NMR in Biomedicine: An International Journal Devoted to the Development and Application of Magnetic Resonance In vivo. Aug. 2009;22(7):745-52.

Hyvärinen et al., Independent component analysis: algorithms and applications. Neural networks. Jun. 1, 2000;13(4-5):411-30.

Kording et al., Dynamic fetal cardiovascular magnetic resonance imaging using Doppler ultrasound gating. Journal of Cardiovascular Magnetic Resonance. Mar. 12, 2018;20(1). 10 pages.

Larson et al., Self-gated cardiac cine MRI. Magnetic Resonance in Medicine: An Official Journal of the International Society for Magnetic Resonance in Medicine. Jan. 2004;51(1):93-102.

Lloyd et al., Three-dimensional visualisation of the fetal heart using prenatal MRI with motion-corrected slice-vol. registration: a prospective, single-centre cohort study. The Lancet. Apr. 20, 2019;393(10181):1619-27.

Lu et al., A semi-automatic method for peak and valley detection in free-breathing respiratory waveforms. Medical physics. Oct. 2006;33(10):3634-6.

Manganaro et al., Potential role of fetal cardiac evaluation with magnetic resonance imaging: preliminary experience. Prenatal Diagnosis: Published in Affiliation With the International Society for Prenatal Diagnosis. Feb. 2008;28(2):148-56.

Meyer-Wittkopf et al., Evaluation of three-dimensional ultrasonography and magnetic resonance imaging in assessment of congenital heart anomalies in fetal cardiac specimens. Ultrasound in Obstetrics

(56) References Cited

OTHER PUBLICATIONS and Gynecology: The Official Journal of the International Society of Ultrasound in Obstetrics and Gynecology. Nov. 1, 1996;8(5):303-8.
Nieman et al., Three-dimensional, in vivo MRI with self-gating and image coregistration in the mouse. Magnetic Resonance in Medicine: An Official Journal of the International Society for Magnetic Resonance in Medicine. May 2009;61(5):1148-57.
Nijm et al., Comparison of self-gated cine MRI retrospective cardiac synchronization algorithms. Journal of Magnetic Resonance Imaging: An Official Journal of the International Society for Magnetic Resonance in Medicine. Sep. 2008;28(3):767-72.
Odille et al., Model-based reconstruction for cardiac cine MRI without ECG or breath holding. Magnetic Resonance in Medicine. May 2010;63(5):1247-57.
Otazo et al., Combination of compressed sensing and parallel imaging for highly accelerated first-pass cardiac perfusion MRI. Magnetic resonance in medicine. Sep. 2010;64(3):767-76.
Paley et al., Fetal electrocardiogram (fECG) gated MRI. Sensors. Aug. 23, 2013;13(9):11271-9.
Roy et al., Accelerated MRI of the fetal heart using compressed sensing and metric optimized gating. Magnetic Resonance in Medicine. 2017;77(6):2125-35.
Roy et al., Dynamic imaging of the fetal heart using metric optimized gating. Magnetic resonance in medicine. Dec. 2013;70(6):1598-607.
Roy et al., Fetal cardiac MRI: a review of technical advancements. Topics in Magnetic Resonance Imaging. Oct. 2019;28(5):235.
Roy et al., Preliminary experience using motion compensated CINE magnetic resonance imaging to visualise fetal congenital heart disease: comparison to echocardiography. Circulation: Cardiovascular Imaging. Nov. 2018;11(12):e007745.
Saleem, Feasibility of MRI of the fetal heart with balanced steady-state free precession sequence along fetal body and cardiac planes. American Journal of Roentgenology. Oct. 2008; 191(4):1208-15.
Sanapo et al., Fetal echocardiography for planning perinatal and delivery room care of neonates with congenital heart disease. Echocardiography. Dec. 2017;34(12):1804-21.
Spraggins et al., Wireless retrospective gating: application to cine cardiac imaging. Magnetic resonance imaging. Jan. 1, 1990;8(6):675-81.
Ueberle et al., Cardiac MR: imaging of the foetal heart dynamics using doppler ultrasound triggering. Biomedical Engineering/Biomedizinische Technik. Aug. 24, 2012;57. 4 pages.
Van Amerom et al., Fetal cardiac cine imaging from motion-corrected super-resolution reconstruction of highly-accelerated real-time MRI. Magnetic Resonance in Medicine. 2018; 79:327-338.
Welch, The use of fast Fourier transform for the estimation of power spectra: a method based on time averaging over short, modified periodograms. IEEE Transactions on audio and electroacoustics. Jun. 1967;15(2):70-3.
Wielandner et al., Potential of magnetic resonance for imaging the fetal heart. Seminars in Fetal and Neonatal Medicine. Oct. 1, 2013;18(5):286-297.
Yamamura et al., Cardiac MRI of the fetal heart using a novel triggering method: initial results in an animal model. Journal of Magnetic Resonance Imaging. May 2012;35(5):1071-6.
Yamamura et al., High resolution MR imaging of the fetal heart with cardiac triggering: a feasibility study in the sheep fetus. European radiology. Oct. 2009; 19:2383-90.
Yerly et al., Coronary endothelial function assessment using self-gated cardiac cine MRI and k-t sparse SENSE. Magnetic resonance in medicine. Nov. 2016;76(5):1443-54.
Zarzoso et al., Robust independent component analysis by iterative maximization of the kurtosis contrast with algebraic optimal step size. IEEE Transactions on neural networks. Feb. 2010;21(2):248-61.

\* cited by examiner

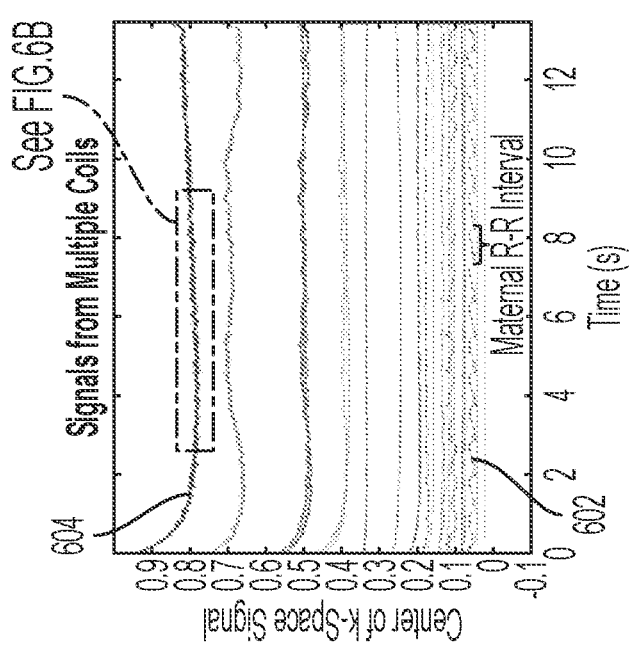
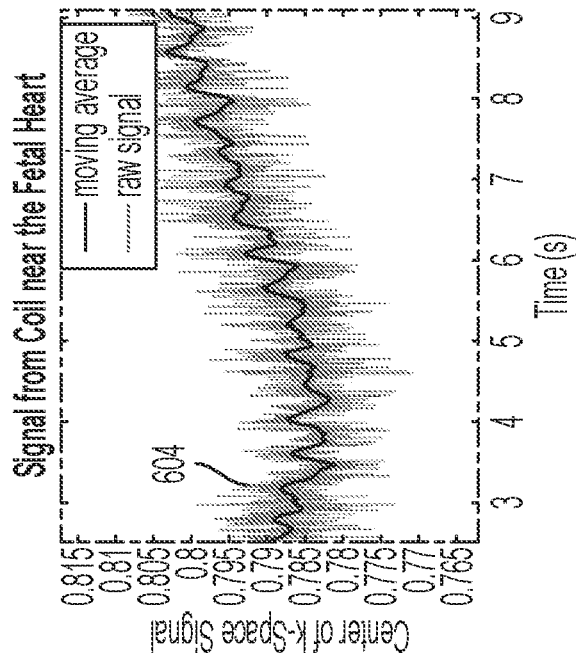
FIG. 6B
FIG. 6A

FETAL CARDIAC MRI USING SELF-GATING WITH A CARTESIAN K-SPACE TRAJECTORY

CROSS-REFERENCE TO RELATED APPLICATIONS

This application is a national stage filing under 35 U.S.C. § 371 of international Patent Application Serial No. PCT/US2021/029116, filed Apr. 26, 2021, which claims priority to U.S. Provisional Patent Application No. 63/016,183, titled "FETAL CARDIAC MRI USING SELF-GATING WITH A CARTESIAN K-SPACE TRAJECTORY", filed Apr. 27, 2020, the entire contents of both of which are incorporated herein by reference.

BACKGROUND

1. Technical Field

Embodiments of the present invention relate to systems and methods for performing cardiac magnetic resonance imaging (MRI). More particularly, in some embodiments, an MR image is generated for a fetus that is disposed within a uterus of a parent of the fetus. In some such embodiments, MR data for a heart of the fetus is analyzed to derive potential cardiac cycles of the fetus that will be used in generating the MR image.

2. Discussion of Related Art

Magnetic resonance imaging (MRI) is a non-invasive and versatile technique for studying the physiology and pathology of biological systems. Generally, MRI operates by detecting magnetic resonance (MR) signals emitted by the nuclei of atoms in a subject in response to changes in magnetic fields and applied electromagnetic radiation (e.g., radio waves). The detected MR signals may then be used to generate MR images of the subject. In particular, new avenues to visualize and evaluate cardiac anatomy and function have been opened through the ability to acquire detailed static and dynamic images of the heart using MRI.

SUMMARY

In one embodiment, there is provided a method of generating a fetal cardiac magnetic resonance (MR) image of a living fetus, within a uterus of a parent of the fetus, by imaging the fetus within the uterus using a magnetic resonance imaging (MRI) system. The method comprises deriving information indicative of cardiac cycles of a heart of the fetus from MR data for the fetus within the uterus, the MR data comprising MR data from a heart of the fetus and from a center of k-space, the MR data being based on data acquired in an imaging of at least the heart of the fetus within the uterus using the MRI system. The method further comprises generating the fetal cardiac MR image based on the information indicative of the cardiac cycles of the heart of the fetus that was derived from the MR data.

In another embodiment, there is provided a method of generating a fetal cardiac MR image of a living fetus, within a uterus of a parent of the fetus, by imaging the fetus within the uterus using an MRI system. The method comprises deriving, from MR data comprising MR data for a heart of the fetus within the uterus, first information indicative of a first potential set of cardiac cycles of the heart of the fetus and second information indicative of a second potential set of cardiac cycles of the heart of the fetus, the MR data being based on data acquired in an imaging of at least the heart of the fetus within the uterus using the MRI system, wherein one of the first information or the second information corresponds to a set of cardiac cycles of the heart of the fetus and the other of the first information or the second information corresponds to a set of cardiac cycles of the heart of the parent. The method further comprises generating at least one fetal cardiac MR image based on information indicative of one potential set of cardiac cycles of the first potential set of cardiac cycles of the heart of the fetus and the second potential set of cardiac cycles of the heart of the fetus.

In another embodiment, there is provided an MRI system configured to generate a fetal cardiac MR image of a living fetus, within a uterus of a parent of the fetus, by imaging the fetus within the uterus. The MRI system comprises a magnetics system configured to, when operated, produce one or more magnetic fields during MR imaging and at least one radio frequency coil configured to, when operated, produce one or more radio frequency pulses during MR imaging. The MRI system further comprises at least one processor configured to receive information indicative of cardiac cycles of a heart of the fetus, the information indicative of the cardiac cycles of the heart of the fetus being based on MR data acquired in an imaging of at least the heart of the fetus within the uterus using the MRI system and to generate the fetal cardiac MR image based on the information indicative of the cardiac cycles of the heart of the fetus that was derived from the MR data.

The foregoing summary is to be considered non-limiting.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 6A is an example of a number of MR signals from the center point of k-space recorded by different radio frequency coils while imaging a fetus within a uterus of the parent using an MRI system;

FIG. 6B is an enlarged view of the MR signal of FIG. 6A from the center point of k-space recorded by a radio frequency coil near the fetal heart;

DETAILED DESCRIPTION

Figure 1:
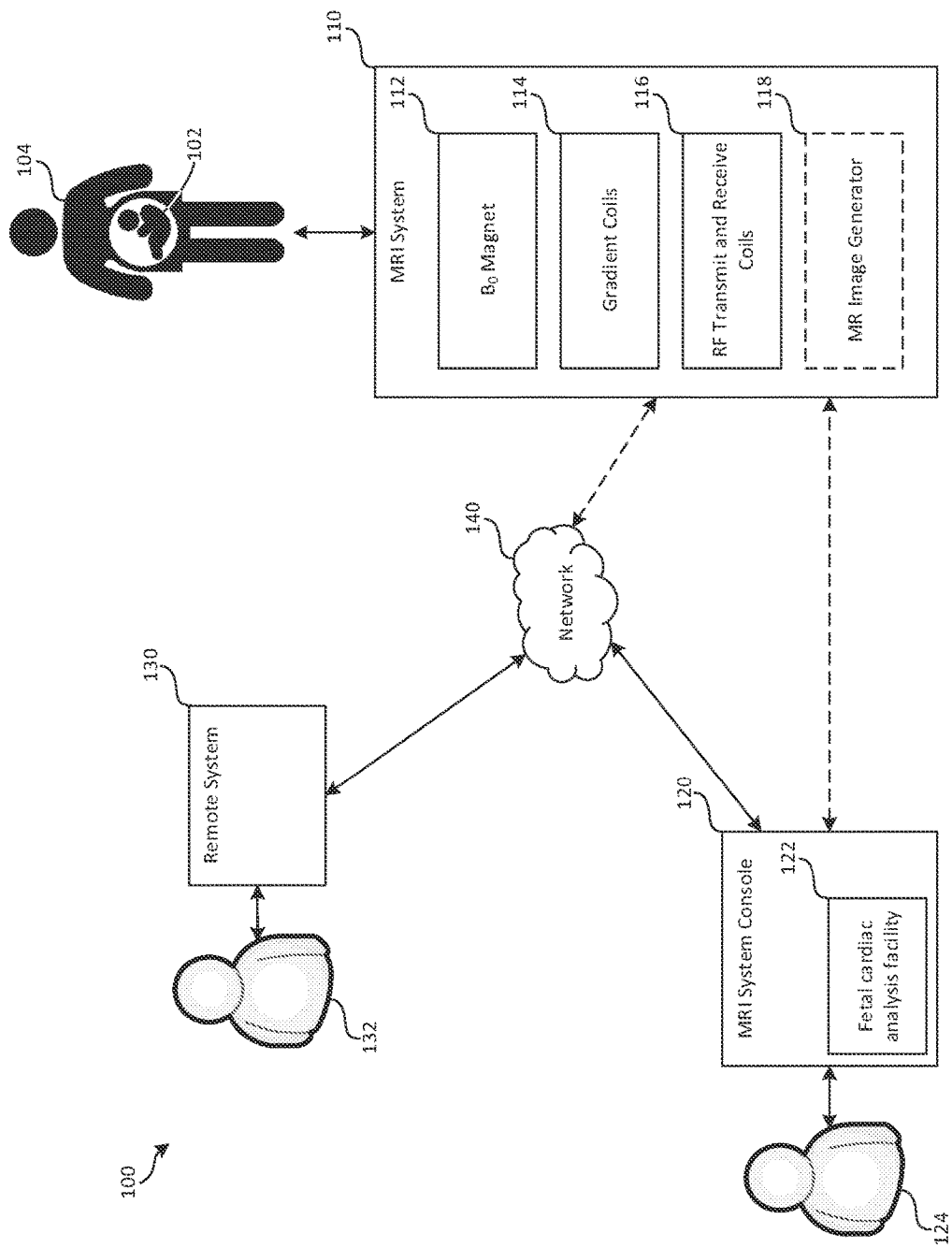
FIG. 1 is a schematic diagram of a magnetic resonance imaging (MRI) facility for performing fetal cardiac MRI, in accordance with some embodiments described herein.

Described herein are techniques for tracking fetal cardiac cycles using cardiac self-gated magnetic resonance imaging (MRI) techniques during an MRI procedure. These techniques include methods of detecting the periodicity of the fetal cardiac cycle from the acquired MR data rather than from data collected from a different device (e.g., external electrodes or ultrasound devices) than the MRI system. Because, in at least some cases, the self-gating signal generated from the fetal heart may be very weak compared to, for example, blood flow in the area of the fetus from parental cardiac motion or measurement noise due to the MRI system itself, described herein are techniques for acquiring, during MR imaging, multiple points from the center of k-space to reduce signal noise as well as methods of using blind source separation to enable the extraction of a reliable fetal self-gating signal from the MR data. In some embodiments described herein, analysis of MR data includes derivation from the MR data of one or more potential sets of cardiac cycles for the fetus, one of which may be the set of cardiac cycles for the fetus and one or more of which may correspond to harmonics for the parent's cardiac cycles. Based on the derived cardiac cycles, one or more MR images of the heart of the fetus are generated.

MRI has been developed into a versatile modality for studying the physiology and pathology of the human cardiovascular system. New avenues to visualize and evaluate cardiac anatomy and function have been opened through the ability to acquire detailed static and dynamic images of the heart. Whereas cardiac MRI has become a part of the clinical imaging portfolio for adult, pediatric, and neonate patients, this imaging modality reaches its technological limits when it comes to assessing the condition of the fetal heart.

Fetal cardiac imaging is important for screening complex congenital heart disease (CHD), which occur at an incidence of approximately five to ten instances per 1000 newborn babies worldwide. Currently, prenatal screening for CHD is performed with ultrasound examinations. However, the sensitivity of fetal cardiac ultrasound varies widely depending on the equipment, national screening policies, level of training, examination practice, and a population of screened patients with CHD. As a result, CHD may remain undetected until birth when using ultrasound examinations as a screening method. Moreover, the evaluation of fetal CHD would benefit from a more precise delineation of CHD morphology in cases where fetal cardiac ultrasound examinations face difficulties such as late gestational age (e.g., greater than 30 gestational weeks), suboptimal fetal position or parental habitus, oligohydramnios, or poor ultrasound windows.

The use of magnetic resonance imaging (MRI) for fetal cardiac imaging provides distinct advantages over ultrasound examinations, given MRI's independence from ultrasound acoustic windows and the ability to measure blood flow circulations. However, since the first attempt more than two decades ago, technical developments in fetal cardiac MRI have remained relatively modest, preventing its translation into clinical practice.

Thus far, cardiac MRI studies of the fetus mostly relied on static and real-time imaging techniques. These techniques may enable only a limited analysis of a fetal heart or cardiac system. Static imaging does not allow for assessment of cardiac function and blood flow, and real-time imaging may have limited spatial and temporal resolution. The inventors have recognized and appreciated that reliably synchronizing the acquisition of magnetic resonance (MR) images with the fetal cardiac cycle so that cardiac motion and blood flow can be resolved remains a significant challenge for fetal cardiac MRI.

Such challenges are similarly faced in post-natal cardiac MR imaging (e.g., of infants, children, and adults), but may be resolved either by: (1) using an outside source of cardiac information to monitor the patient's heart rate or, (2) by using the MR data acquired by the MRI system to determine the relevant cardiac information (e.g., for self-gating of the MR data).

The first technique may not easily be applied to fetuses that are in situ within a uterus of a parent. There have been several attempts to use MR-compatible cardiotocographs, electrodes, and/or Doppler ultrasound devices to detect the heartbeat of the fetal heart. However, cardiotocograph and Doppler ultrasound devices often need to be repositioned during MR imaging as the fetus moves and are thus not well-suited for clinical applications. Additionally, electrode-based devices can interfere with gradient magnetic fields used during MRI and are prone to errors in tracking the cardiac cycle. For a fetus, then, there may be limited additional cardiac information that can be used to generate a clinically-useful fetal cardiac MR image.

For the second technique, fetal cardiac MRI presents additional challenges that are not faced by post-natal cardiac MRJ. For example, cardiac motion from the parent's cardiac cycle can introduce an additional signal source that is not present in post-natal cardiac MRJ. This additional signal source may obscure the fetus' cardiac cycle due to the relative sizes of the parental and fetal hearts and the corresponding motion and/or because the fetal heart may be further from a radio frequency detection coil than the parental heart. Fetal motion may also introduce additional MR signal noise sources that reduce MR image quality. For these reasons, extracting the fetal cardiac cycle from acquired MR data poses significant challenges for generating clinically-useful fetal cardiac MR images.

The inventors have accordingly developed systems and methods for determining the cardiac cycles of a heart of a fetus (referred to herein as a "fetal cardiac cycles") based on MR data acquired by an imaging of the fetus within a uterus of a parent by an MRI system. The inventors have further developed systems and methods for generating a fetal cardiac MR image based on at least the determined fetal cardiac cycle. In some embodiments, the method includes deriving information indicative of the fetal cardiac cycles from MR data acquired of the fetus within the uterus. A cardiac cycle may be, for example, a duration of the fetal heartbeat, which may be used to determine the duration of the four cardiac phases within the heartbeat.

In some embodiments, the MR data, in addition to comprising MR data from the fetal heart, may comprise MR data acquired from a center of k-space by the MRI system. Because k-space is a Fourier transform of the MR image, each point in k-space contains spatial frequency and phase information about every pixel in a final generated MR image. The center of k-space corresponds to the constant term in the Fourier representation of the MR image, and accordingly contributes primarily to overall image contrast and brightness. The center of k-space may be a point where $k_x=k_y=0$, and, for example, for some Cartesian MR signal acquisition schemes may be acquired with no phase-encoding gradient magnetic field applied to the patient. In some embodiments, the center of k-space may be sampled multiple times during each repetition period in order to increase the signal-to-noise ratio (SNR) in the MR data.

In some embodiments, the method may include generating the fetal cardiac MR image based on the information indicative of the fetal cardiac cycle that was derived from the MR data. Based on the determined information indicative of the fetal cardiac cycle, MR data instances of the MR data may be grouped based on when the MR data instances were acquired relative to the fetal cardiac cycle. For example, the MR data instances may be grouped into one of a number of cardiac phases (e.g., diastole and/or systole). The fetal cardiac MR image may then, in some embodiments, be generated by selecting a cardiac phase and generating (e.g., reconstructing) the fetal cardiac MR image based on the MR data instances grouped into the selected cardiac phase.

In some embodiments, rather than determining information indicative of a single set of fetal cardiac cycles, the method may determine information indicative of two potential sets of fetal cardiac cycles. One of the two potential sets of fetal cardiac cycles may correspond, for example, to the actual fetal cardiac cycles while the other potential set of fetal cardiac cycles may correspond to the parental cardiac cycles (e.g., a harmonic frequency of the parental cardiac cycles). In such embodiments, the method may include deriving, from MR data comprising MR data for a heart of the fetus within the uterus, first information indicative of a first set of potential fetal cardiac cycles and second information indicative of a second set of potential fetal cardiac cycles. The MR data may be based on data acquired in an imaging of at least the heart of the fetus within the uterus using the MRI system.

In some embodiments, generating the fetal cardiac MR image may comprise generating, as described herein, at least one fetal cardiac MR image based on one of the first potential set of fetal cardiac cycles and the second set of potential fetal cardiac cycles. For example, a fetal cardiac MR image may be generated based on whichever of the first and second potential fetal cardiac cycles is most likely to be the actual fetal cardiac cycle. In some embodiments, two fetal cardiac MR images may be generated, each corresponding to one of the first and second sets of potential fetal cardiac cycles, so that a clinician may review the two fetal cardiac MR images.

The inventors have further developed an MRI system configured to generate a fetal cardiac MR image of a living fetus, within a uterus of a parent of the fetus, by imaging the fetus within the uterus. In some embodiments, the MRI system includes a magnetics system configured to produce one or more magnetic fields during MR imaging and at least one radio frequency coil configured to produce one or more radio frequency pulses during MR imaging. The MRI system may further include at least one processor configured to receive information indicative of a fetal cardiac cycle, the information indicative of the fetal cardiac cycle being based on MR data acquired in an imaging of at least the heart of the fetus within the uterus using the MRI system. The at least one processor may be further configured to generate the fetal cardiac MR image based on the information indicative of the fetal cardiac cycles that were derived from the MR data, as described herein.

FIG. 1 is a block diagram of an example of an MRI facility 100 for performing fetal cardiac MRI, in accordance with some embodiments described herein. In the illustrative example of FIG. 1, MRI facility 100 includes an MRI system 110, an MRI system console 120, and a remote system 130. It should be appreciated that MRI facility 100 is illustrative and that an MRI facility may have one or more other components of any suitable type in addition to or instead of the components illustrated in FIG. 1. For example, there may be additional remote systems (e.g., two or more) present within an MRI facility.

As illustrated in FIG. 1, in some embodiments, one or more of the MRI system 110, the MRI system console 120, and the remote system 130 may be communicatively connected by a network 140. The network 140 may be or include one or more local- and/or wide-area, wired and/or wireless networks, including a local-area or wide-area enterprise network and/or the Internet. Accordingly, the network 140 may be, for example, a hard-wired network (e.g., a local area network within a facility), a wireless network (e.g., connected over Wi-Fi and/or cellular networks), a cloud-based computing network, or any combination thereof. For example, in some embodiments, the MRI system 110 and the MRI system console 120 may be located within a same facility and connected directly to each other or connected to each other via the network 140, while the remote system 130 may be located in a remote facility and connected to the MRI system 110 and/or the MRI system console 120 through the network 140.

In some embodiments, the MRI system 110 may be configured to perform MR imaging of a living fetus 102 within a uterus of a parent 104. While FIG. 1 illustrates the parent and fetus as humans and some embodiments may be adapted to work with humans, other embodiments are not so limited. Some embodiments may operate with other species in which a parent gestates a developing fetus, including other species of mammals. For example, the MRI system 110 may include a $B_0$ magnet 112, gradient coils 114, and radio frequency (RF) transmit and receive coils 116 configured to act in concert to perform said MR imaging.

In some embodiments, $B_0$ magnet 112 may be configured to generate the main static magnetic field, $B_0$, during MR imaging. The $B_0$ magnet 112 may be any suitable type of magnet that can generate a static magnetic field for MR imaging. For example, the $B_0$ magnet 112 may include a superconducting magnet, an electromagnet, and/or a permanent magnet. In some embodiments, the $B_0$ magnet 112 may be configured to generate a static magnetic field having a particular field strength. For example, the $B_0$ magnet 112 may be a magnet that can generate a static magnetic field having a field strength of 1.5 T, or, in some embodiments, a field strength greater than or equal to 1.5 T and less than or equal to 3.0 T.

In some embodiments, gradient coils 114 may be arranged to provide one or more gradient magnetic fields. For example, gradient coils 114 may be arranged to provide gradient magnetic fields along three substantially orthogonal directions (e.g., x, y, and z). The gradient magnetic fields may be configured to, for example, provide spatial encoding of MR signals during MR imaging. Gradient coils 114 may comprise any suitable electromagnetic coils, including discrete wire winding coils and/or laminate panel coils.

In some embodiments, RF transmit and receive coils 116 may be configured to generate RF pulses to induce an oscillating magnetic field, $B_1$, and/or to receive MR signals from nuclear spins of the imaged subject (e.g., of the fetus 102) during MR imaging. The RF transmit coils may be configured to generate any suitable types of RF pulses useful for performing fetal cardiac MR imaging. RF transmit and receive coils 116 may comprise any suitable RF coils, including volume coils and/or surface coils.

In some embodiments, the MRI system 110 may optionally include MR image generator 118. MR image generator 118 may be configured to generate MR images based on MR data acquired by the MRI system 110 during MR imaging of the fetus 102. For example, in some embodiments, MR image generator 118 may be configured to perform MR image reconstruction to generate MR images in the image domain based on MR data in the spatial frequency domain (e.g., MR data comprising data describing k-space).

As illustrated in FIG. 1, MRI facility 100 includes MRI system console 120 communicatively coupled to the MRI system 110. MRI system console 120 may be any suitable electronic device configured to send instructions and/or information to MRI system 120, to receive information from MRI system 120, and/or to process obtained MR data. In some embodiments, MRI system console 120 may be a fixed electronic device such as a desktop computer, a rack-mounted computer, or any other suitable fixed electronic device. Alternatively, MRI system console 120 may be a portable device such as a laptop computer, a smart phone, a tablet computer, or any other portable device that may be configured to send instructions and/or information to MRI system 120, to receive information from MRI system 120, and/or to process obtained MR data.

Some embodiments may include a fetal cardiac analysis facility 122. Fetal cardiac analysis facility 122 may be configured to analyze MR data obtained by MRI system 110 from an MR imaging procedure of fetus 102. Fetal cardiac analysis facility 122 may be configured to, for example, analyze the obtained MR data by determining one or more potential sets of fetal cardiac cycles from the MR data, as described herein. Fetal cardiac analysis facility 122 may be implemented as hardware, software, or any suitable combination of hardware and software, as aspects of the disclosure provided herein are not limited in this respect. As illustrated in FIG. 1, the fetal cardiac analysis facility 122 may be implemented in the MRI system console 120, such as by being implemented in software (e.g., executable instructions) executed by one or more processors of the MRI system console 120. However, in other embodiments, the fetal cardiac analysis facility 122 may be additionally or alternatively implemented at one or more other elements of the system 100 of FIG. 1. For example, the fetal cardiac analysis facility 122 may be implemented at the MRI system 110 and/or the remote system 130 discussed below. In other embodiments, the fetal cardiac analysis facility 122 may be implemented at or with another device, such as a device located remote from the system 100 and receiving data via the network 140.

MRI system console 120 may be accessed by MRI user 124 in order to control MRI system 120 and/or to process MR data obtained by MRI system 120. For example, MRI user 124 may implement an MR imaging process by inputting one or more instructions into MRI system console 120 (e.g., MRI user 124 may select an MR imaging process from among several options presented by MRI system console 120). Alternatively or additionally, in some embodiments, MRI user 124 may implement an MR data analysis procedure by inputting one or more instructions into MRI system console 120 (e.g., MRI user 124 may select MR data instances to be analyzed by MRI system console 120).

As illustrated in FIG. 1, MRI system console 120 also interacts with remote system 130 through network 140, in some embodiments. Remote system 130 may be any suitable electronic device configured to receive information (e.g., from MRI system 110 and/or MRI system console 120) and to display generated MR images for viewing. The remote system 130 may be remote from the MRI system 110 and MRI system console 120, such as by being located in a different room, wing, or building of a facility (e.g., a healthcare facility) than the MRI system 110, or being geographically remote from the system 110 and console 120, such as being located in another part of a city, another city, another state or country, etc. In some embodiments, remote system 130 may be a fixed electronic device such as a desktop computer, a rack-mounted computer, or any other suitable fixed electronic device. Alternatively, remote system 130 may be a portable device such as a laptop computer, a smart phone, a tablet computer, or any other portable device that may be configured to receive and view generated MR images and/or to send instructions and/or information to MRI system console 120.

In some embodiments, remote system 130 may receive information (e.g., MR data analysis results, generated fetal cardiac MR images) from MRI system console 120 and/or MRI system 110 over the network 140. A remote user 132 (e.g., the parent's medical clinician) may use remote system 130 to view the received information on remote system 130. For example, the remote user 132 may view generated fetal cardiac MR images using remote system 130 after the MRI user 124 has completed MR data analysis using MRI system 110 and/or MRI system console 120.

Figure 2:
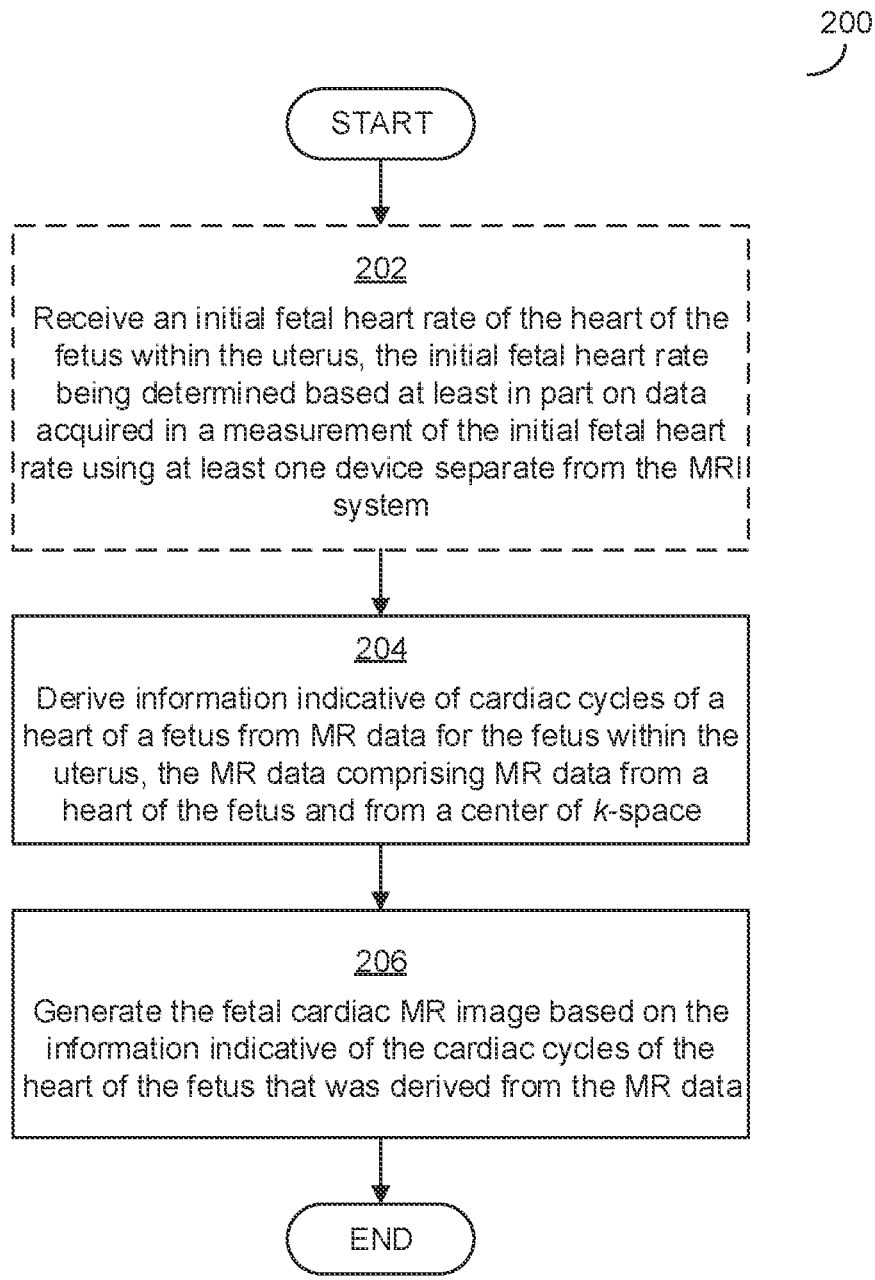
FIG. 2 is a flowchart of an illustrative process 200 of generating a fetal cardiac MR image, in accordance with some embodiments described herein.

FIG. 2 is a flowchart of an illustrative process 200 of generating a fetal cardiac MR image, in accordance with some embodiments described herein. Process 200 may be implemented by a fetal cardiac analysis facility, such as the facility 122 of FIG. 1. As such, in some embodiments, the process 200 may be performed by a computing device configured to send instructions to an MRI system and/or to receive information from an MRI system (e.g., MRI system console 120 executing fetal cardiac analysis facility 122 as described in connection with FIG. 1). As another example, in some embodiments, the process 200 may be performed by one or more processors located remotely (e.g., as part of a cloud computing environment, as connected through a network) from the MRI system that obtained the input MR data.

Process 202 may begin optionally at act 202, where the fetal cardiac analysis facility receives an initial fetal heart rate of the heart of the fetus. In some embodiments, the initial fetal heart rate may be determined based on, at least in part, data acquired in a measurement using a device separate from the MRI system. For example, the data may be acquired in a measurement performed by using an ultrasound device separate from the MRI system. Such fetal heart rate measurements may be performed prior to performing an MR imaging procedure, in some embodiments.

At act 204, the fetal cardiac analysis facility may derive information indicative of fetal cardiac cycles from MR data of the living fetus within a uterus of the parent. The MR data may have been obtained by an MRI system (e.g., MRI system 110) performing an MR imaging procedure of a heart of the fetus. Additionally, the MR data may comprise MR data acquired from the center of k-space. For example, in some embodiments, the MRI system may implement a pulse sequence configured to sample the center of k-space multiple times (e.g., greater than 50 times, greater than 100 times, in a range from 50 to 200 times) during a repetition time (TR) of the pulse sequence. In some embodiments, the pulse sequence may be configured to sample the center of k-space multiple times during each TR of the pulse sequence. In some embodiments, the pulse sequence may be a steady-state free precession (SSFP) pulse sequence and/or a balanced SSFP pulse sequence.

In some embodiments, the fetal cardiac analysis facility may derive information indicative of fetal cardiac cycles from the MR data by using blind source separation (BSS) to extract one or more fetal cardiac motion signals from the MR data, as described herein. The obtained MR data may comprise information from several sources of motion (e.g., fetal cardiac motion, fetal motion, parental cardiac motion, parental breathing, etc.). The fetal cardiac analysis facility may use BSS to recover a set of these source signals from a set of observed signal mixtures within the MR data in order to separate the multiple potential sources of motion signals. In some embodiments, the fetal cardiac analysis facility may use independent component analysis (ICA) or second-order blind identification (SOBI) to perform BSS and extract information indicative of fetal cardiac cycles from the MR data.

In some embodiments, after extracting one or more fetal cardiac motion signals from the MR data using BSS, the fetal cardiac analysis facility may determine which of the one or more fetal cardiac motion signals represents a potential fetal cardiac motion signal for use in generating a fetal cardiac MR image. The fetal cardiac analysis facility may calculate a power spectral density of each of the one or more fetal cardiac motion signals. The fetal cardiac analysis facility may then, in some embodiments, identify one or more maxima within each of the calculated power spectral densities, and may do so by analyzing one or more local maxima within one or more subset ranges of the power spectral densities. The subset range(s) may correspond to heart rate values. For example, the subset range may be centered around the initial fetal heart rate determined in act 202 or, in some embodiments, the subset range may be centered around a guessed fetal heart rate. The subset range may be, for example, 30 bpm in width (e.g., ±15 bpm around the centered value of the subset range). The fetal cardiac analysis facility may determine, from the local maxima found within the subset range, one or more average fetal heart rates based on the corresponding frequencies of each local maxima peak.

After deriving information indicative of fetal cardiac cycles in act 204, the process may proceed to act 206, in some embodiments. In act 206, the fetal cardiac analysis facility may generate the fetal cardiac MR image based on the information indicative of the fetal cardiac cycles that was derived from the MR data. In some embodiments, generating the fetal cardiac MR image may comprise reconstructing the fetal cardiac MR image (e.g., reconstructing the fetal cardiac MR image in the image domain based on MR data in k-space).

In some embodiments, generating the fetal cardiac MR image may further comprise using the information indicative of the fetal cardiac cycles to group MR data instances into a plurality of time periods related to the cardiac phases (e.g., diastole, systole) of the fetal heart. Grouping the MR data instances into the plurality of cardiac phases (e.g., gating the MR data) enables generation of fetal cardiac MR images for specific cardiac phases and reduces cardiac-motion-related noise in the resulting fetal cardiac MR images. Generating the fetal cardiac MR image may thus include selecting a desired cardiac phase and generating the fetal cardiac MR image based on the grouped MR data instances correlated with the selected cardiac phase.

In some embodiments, the MRI system used to scan the parent and fetus and to generate the MR data (e.g., MRI system 110 of FIG. 1) may include an image generator (e.g., MR image generator 118 of FIG. 1) that is used for generating images from MR data for scan. This built-in image generator may be used for generating MR images for patients that have been imaged with the MR system for purposes other than fetal cardiac analysis. In some such embodiments, the fetal cardiac facility may not use the built-in image generator of the MRI system (e.g., not use the MR image generator 118 of FIG. 1), but may instead include its own image generator for adapting MR data from the imaging of fetus 102 into one or more MR images. This may be because of the challenges of generating a fetal cardiac MR image, as discussed above, which the built-in image generator may not be specifically adapted for. In such embodiments, the fetal cardiac analysis facility may use known techniques for generating an MR image from MR data, to adapt the fetal cardiac MR data into an MR image, and to do so may analyze the MR data together with information for the potential fetal cardiac cycle, such as timing information.

However, in other embodiments, the built-in MR image generator of the MRI system may be leveraged for generating fetal cardiac MR images. In such a case, the built-in MR image generator may be configured to receive as an input cardiac cycle information and to use that cardiac cycle information to generate MR images from cardiac MR data. To generate the fetal cardiac MR image(s), the fetal cardiac analysis facility may calculate one or more potential fetal cardiac cycles and, for each potential fetal cardiac cycle, provide an indication of the potential fetal cardiac cycle to the built-in MR image generator. Providing the indication of the potential fetal cardiac cycle to the built-in MR image generator may include providing timing information on the potential fetal cardiac cycle to the built-in MR image generator. The built-in MR image generator may then analyze the MR data for the imaging of the fetus 102 together with the received indication of the potential fetal cardiac cycle to generate a fetal cardiac MR image, using the built-in techniques of the built-in MR image generator for adapting MR data into an MR image.

In block 204 of the example of FIG. 2, the facility was described as deriving information indicative of one or more potential fetal cardiac signals. In some embodiments, a single potential fetal cardiac signal may be generated. In other embodiments, two or more potential fetal cardiac signals may be derived, which in some such embodiments may then be analyzed to determine which of the potential fetal cardiac signals may be an accurate fetal cardiac signal.

In some such embodiments that derive multiple potential fetal cardiac signals, the multiple signals may represent accurate and/or erroneous cardiac signals in any suitable manner. In some cases, one potential set of cardiac cycles may correspond to cardiac cycles for the parent in which the fetus is disposed while another may correspond to cardiac cycles for the fetus. In some instances the fetal heartrate may have a frequency similar to that of a harmonic of the parental heartrate (e.g., the second harmonic of the parental heartrate). Deriving two sets of information and/or generating two fetal cardiac MR images may ensure that a fetal cardiac MR image is generated based on the actual fetal cardiac cycles rather than a harmonic of the parental cardiac cycles.

Figure 3:
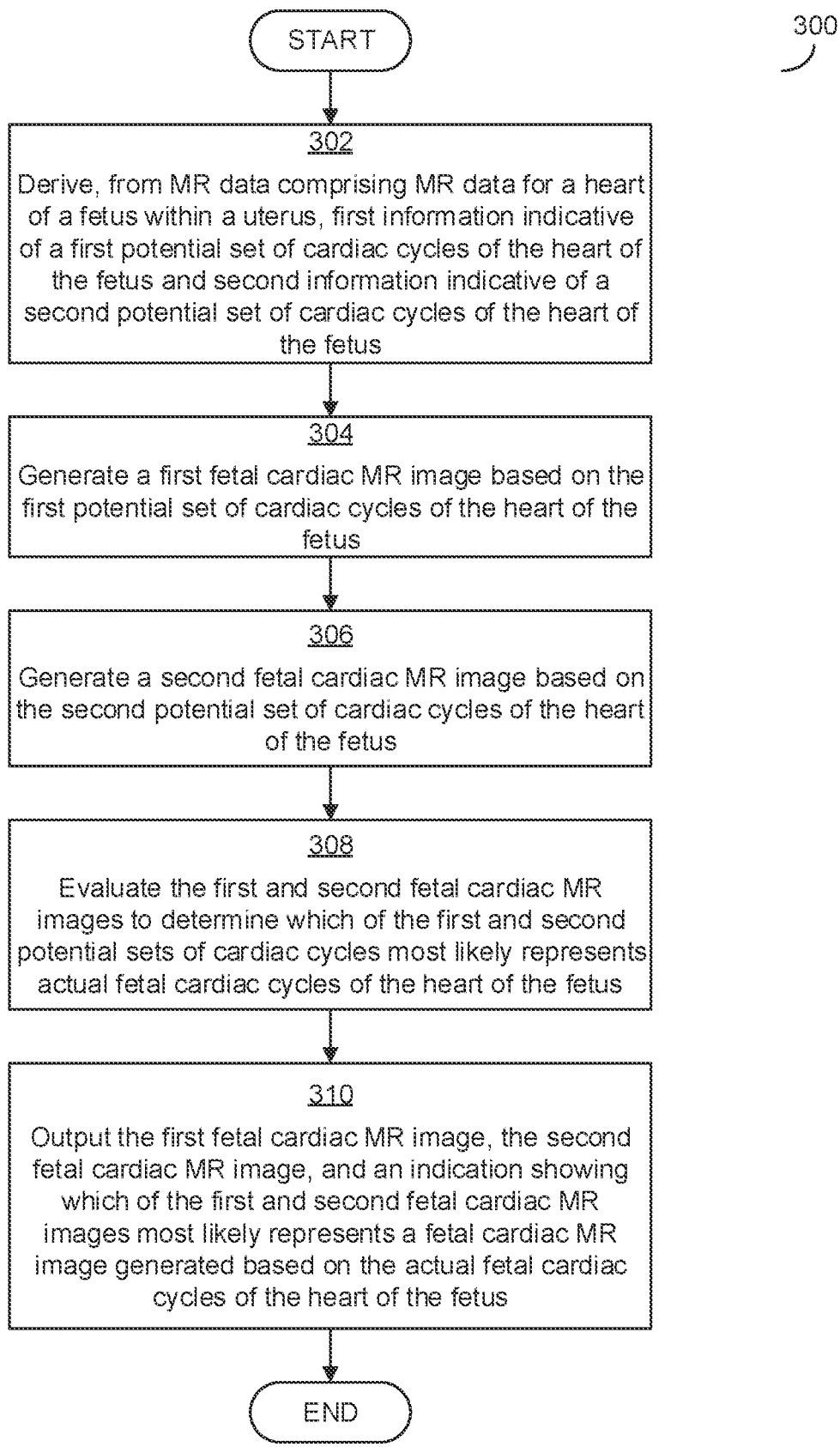
FIG. 3 is a flowchart of an illustrative process 300 of generating a fetal cardiac MR image, in accordance with some embodiments described herein.

FIG. 3 is a flowchart of an illustrative process 300 of generating a fetal cardiac MR image, in accordance with some embodiments described herein. Process 300 may be implemented by a fetal cardiac analysis facility, such as the facility 122 of FIG. 1. As such, in some embodiments, the process 300 may be performed by a computing device configured to send instructions to an MRI system and/or to receive information from an MRI system (e.g., MRI system console 120 executing fetal cardiac analysis facility 122 as described in connection with FIG. 1). As another example, in some embodiments, the process 300 may be performed by one or more processors located remotely (e.g., as part of a cloud computing environment, as connected through a network) from the MRI system that obtained the input MR data.

For ease of description, the process 300 will be described in connection with generating two sets of information and two images, but it should be appreciated the embodiments are not limited to operating with only two potential sets of cardiac cycles and that some embodiments may operate with more than two potential sets of cardiac cycles.

In some embodiments, process 300 may begin at act 302, in which the fetal cardiac analysis facility may derive, from MR data of a heart of a fetus within a uterus, first and second information. The first information may be indicative of a first potential set of fetal cardiac cycles, and the second information may be indicative of a second potential set of fetal cardiac cycles. As discussed above, in some embodiments, the first potential set of fetal cardiac cycles may relate to a parent and the second potential set of fetal cardiac cycles may relate to the fetus, though embodiments are not so limited.

In some embodiments, the fetal cardiac analysis facility may derive the first information indicative of the first potential set of fetal cardiac cycles and the second information indicative of the second potential set of fetal cardiac cycles from the MR data by using blind source separation (BSS) to extract one or more potential fetal cardiac motion signals from the MR data, as described herein. In some embodiments, the MR data may have been obtained by an MRI system (e.g., MRI system 110) performing an MR imaging procedure of a heart of the fetus. The obtained MR data may comprise information from several sources of motion (e.g., fetal cardiac motion, fetal motion, parental cardiac motion, parental breathing, etc.). The fetal cardiac analysis facility may use BSS to recover a set of these source signals from a set of observed signal mixtures within the MR data in order to separate the multiple potential sources of motion signals. In some embodiments, the computing system may use independent component analysis (ICA) or second-order blind identification (SOBI) to perform BSS and extract the first and second information indicative of first and second potential fetal cardiac cycles from the MR data.

In some embodiments, after extracting one or more fetal and/or parental cardiac motion signals from the MR data using BSS, the fetal cardiac analysis facility may determine which two of the one or more fetal cardiac motion signals represents a first and second potential fetal cardiac motion signal for use in generating the fetal cardiac MR images. The fetal cardiac analysis facility may calculate a power spectral density of each of the one or more fetal and/or parental cardiac motion signals. The fetal cardiac analysis facility may then, in some embodiments, identify local maxima of each of the calculated power spectral densities within a subset range of heart rate values. The subset range may be centered around a known value of the fetal heart rate (e.g., as determined by a previous measurement). In some embodiments, the subset range may be centered around a guessed fetal heart rate. The subset range may be, for example, 30 bpm in width (e.g., ±15 bpm around the centered value of the subset range). The fetal cardiac analysis facility may determine, from the local maxima found within the subset range, a first and second average fetal heart rate based on corresponding frequencies of the two most intense local maxima within the subset range.

The process 300 may then move to act 304, in which the fetal cardiac analysis facility or the MRI system (e.g., MRI system 110) may generate a first fetal cardiac MR image based on the first potential set of fetal cardiac cycles. In some embodiments, generating the first fetal cardiac MR image may comprise using the information indicative of the first potential set of fetal cardiac cycles to group MR data instances into a plurality of time periods related to the first potential cardiac phases (e.g., diastole, systole) of the fetal heart. Generating the first fetal cardiac MR image may then include selecting a desired cardiac phase and generating the first fetal cardiac MR image based on the first grouped MR data instances correlated with the selected cardiac phase.

The process 300 may then move to act 306, in which the fetal cardiac analysis facility or the MRI system (e.g., MRI system 110) may generate a second fetal cardiac MR image based on the second potential set of fetal cardiac cycles. In some embodiments, generating the second fetal cardiac MR image may comprise using the information indicative of the second potential set of fetal cardiac cycles to group MR data instances into a plurality of time periods related to the second potential cardiac phases (e.g., diastole, systole) of the fetal heart. Generating the second fetal cardiac MR image may then include selecting a desired cardiac phase and generating the second fetal cardiac MR image based on the second grouped MR data instances correlated with the selected cardiac phase.

In some embodiments, once the images are generated, the images may be output for review by a clinician or other user, who may determine which of the images is based on the best reflection of or the accurate reflection of the fetus' cardiac cycle and which is therefore the most accurate MR image for the fetus. In other embodiments, however, including the embodiment of FIG. 3, the fetal cardiac analysis facility may evaluate the cardiac cycles and/or the images to identify which is most likely the accurate cardiac cycle for the fetus.

Accordingly, after generating the first and second fetal cardiac MR images, the process 300 may move to act 308, in which the fetal cardiac analysis facility may evaluate the first and second fetal cardiac MR images. Evaluating the first and second fetal cardiac MR images may comprise determining which of the first and second potential sets of cardiac cycles is most likely the actual fetal cardiac cycles or is the better reflection of the actual fetal cardiac cycle, or of which of the first and second fetal cardiac MR images was generated based on cardiac cycles that are most likely to be or are the best reflection of the actual fetal cardiac cycles. This determination may comprise, for example, an image analysis of the image data for the MR images. For example, the facility may determine from an analysis of image data which of the first and second fetal cardiac MR images has higher contrast or less blurring, which may indicate the use of more accurate fetal cardiac signals in generating the fetal cardiac MR image.

Once the fetal cardiac analysis facility has evaluated the first and second fetal cardiac MR images, the process 300 may move to act 310, in which the first and second fetal cardiac MR images are output by the fetal cardiac analysis facility. In some embodiments, the fetal cardiac analysis facility may also output an indication of which of the first and second fetal cardiac MR images was most likely generated based on the actual fetal cardiac cycles of the heart of the fetus, as determined in act 308. In some embodiments, the fetal cardiac analysis facility may output the first and second fetal cardiac MR images and the indication to a user display (e.g., a screen) for viewing, or the fetal cardiac analysis facility may output the first and second fetal cardiac MR images and the indication by transmitting them to another computing system (e.g., remote system 130) or storing them either locally or remotely (e.g., via cloud computing).

While in some embodiments, both the first and second fetal cardiac MR images and the indication are output by the fetal cardiac analysis facility, embodiments are not so limited. In some embodiments, once the facility makes a determination of which MR image was most likely generated for the actual fetal cardiac cycle or a best reflection of the actual fetal cardiac cycle, only that image may be output and the other image(s) may not be output. The other image(s) may be discarded in some embodiments, or alternatively may be stored by the facility or another system and may be retrieved upon request (to the fetal cardiac analysis facility or such other system) from a user (e.g., a clinician) for the alternative images(s).

Figure 4:
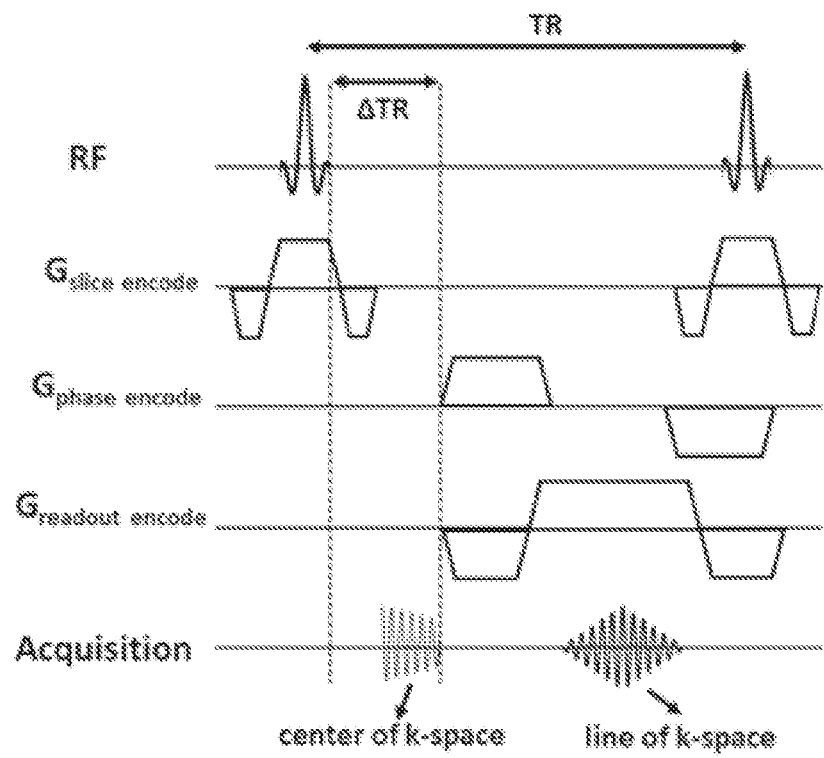
FIG. 4 is an illustrative example of a pulse sequence for performing fetal cardiac MRI, in accordance with some embodiments described herein.

FIG. 4 is an illustrative example of a SSFP pulse sequence for performing fetal cardiac MRI, in accordance with some embodiments described herein. The phase- and readout-encoding gradients, $G_{phase\ encode}$ and $G_{readout\ encode}$, are delayed for a time $\Delta TR$ to read out the center of k-space, as shown in the Acquisition line. The repetition time (TR) may be extended from 2.8 ms to 3.7 ms to sample the center point of k-space multiple times (e.g., greater than 50, between 50 and 200, and 200 times) before measuring each line of k-space with a Cartesian trajectory. The measured center points of k-space may be processed using a method of blind source separation (BSS) and utilized to detect cardiac cycles. The measured k-space line in each TR may then assigned to appropriate cardiac phases based on the detected cardiac cycles.

The SSFP pulse sequence of FIG. 4 may be configured to measure the center point of k-space before reading a line of k-space in each TR. To measure the center point of k-space multiple times, the distance between the slice-encode prewinding gradient and the phase-encode gradient may be extended by a time $\Delta TR$ (e.g., ≈1 ms). During this time, multiple samples from the center point of k-space are sampled and averaged to reduce the noise in the MR measurements. The center points of k-space may then processed using a BSS method (e.g., second order blind identification (SOBI) and/or independent component analysis (ICA)), to detect the fetal cardiac cycles.

Figure 5:
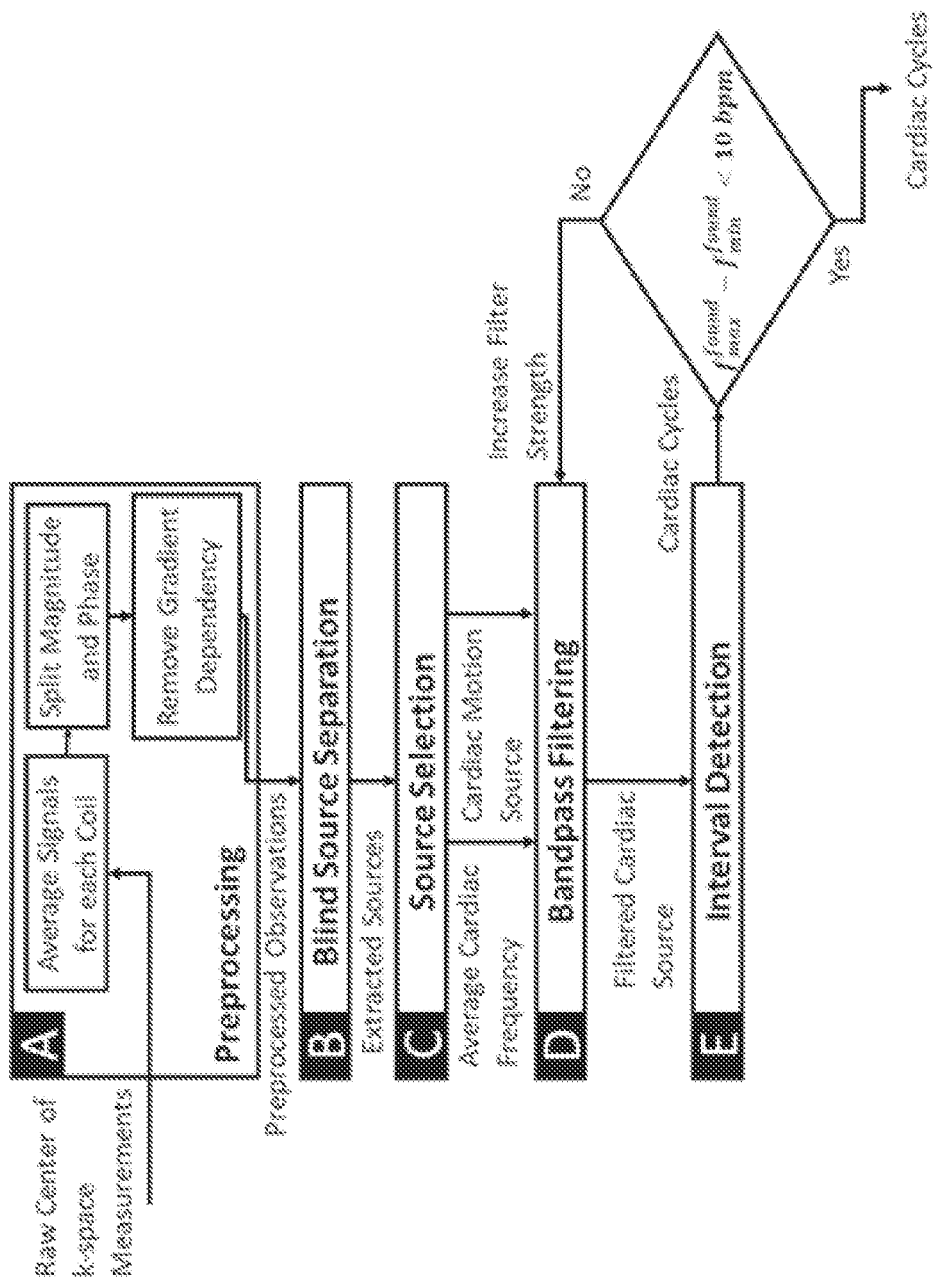
FIG. 5 is a flowchart describing a process 500 for determining one or more cardiac cycles of a fetus based on magnetic resonance (MR) data obtained by imaging the fetus within a uterus of a parent using an MRI system, in accordance with some embodiments described herein.

FIG. 5 is a flowchart describing a process 500 for determining one or more cardiac cycles of a fetus based on magnetic resonance (MR) data obtained by imaging the fetus within a uterus of a parent using an MRI system, in accordance with some embodiments described herein. The process 500 includes five steps: A) preprocessing, B) blind source separation, C) cardiac component selection, D) bandpass filtering, and E) peak or interval detection.

In some embodiments, the computing system may preprocess raw center-of-k-space measurements in act (A) before separating different motion sources from the noise using a BSS algorithm in act (B). Afterwards, the computing system may identify potential fetal cardiac components based on their power spectrum in act (C). The computing system may bandpass filter each cardiac component around the determined average cardiac frequency in act (D), and the cardiac cycles may be determined based on the peaks detected by the moving-average-crossing algorithm in act (E). The computing system may determine the maximum and minimum fetal heart rates thereafter, and if the difference is greater than 10 bpm, the bandpass filter strength may be increased. Acts (D) and (E) may be repeated until the difference is less than 10 bpm.

In act (A), the multiple points sampled from the center of k-space at each TR may be averaged to minimize the measurement noise of the MR data. Magnitude and phase information may then be split and treated as separate observations. The center points of k-space may be concatenated to generate an $2N_c \times N_t$ observation matrix, where $N_c$ is the number of coils and $N_t$ is the number of TRs in a single slice 2D cine SSFP acquisition. The center points of k-space may then be compensated for a phase-encoding gradient dependency by subtracting a least-squares fit of a straight line with respect to the phase-encoding gradient.

FIG. 6A is an example of a number of MR signals measured from the center point of k-space as recorded by different radio frequency coils of a multiple phase-array coil while imaging a fetus within a uterus of the parent using an MRI system. The signals were acquired while using a 2D cine SSFP pulse sequence in a short-axis view of a pregnant volunteer. The parental heartbeat may already be identified from the raw time signals derived from one coil near the parental heart, as seen in the signal 602 of FIG. 6A.

FIG. 6B is an enlarged view of the uppermost MR signal 604 of FIG. 6A from the center point of k-space recorded by a radio frequency coil near the fetal heart. The fetal heart rate may be identified from the signal 604 produced by this radio frequency coil near the fetal heart.

Figure 6D:
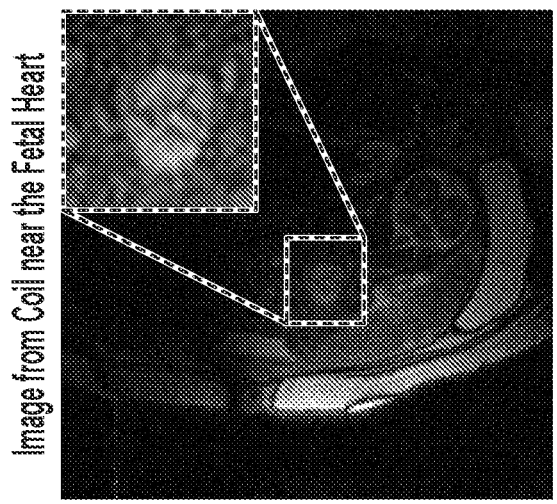
FIG. 6D is an example of an MR image generated from MR signals recorded by a radio frequency coil near the fetal heart, in short-axis view.
Figure 6C:
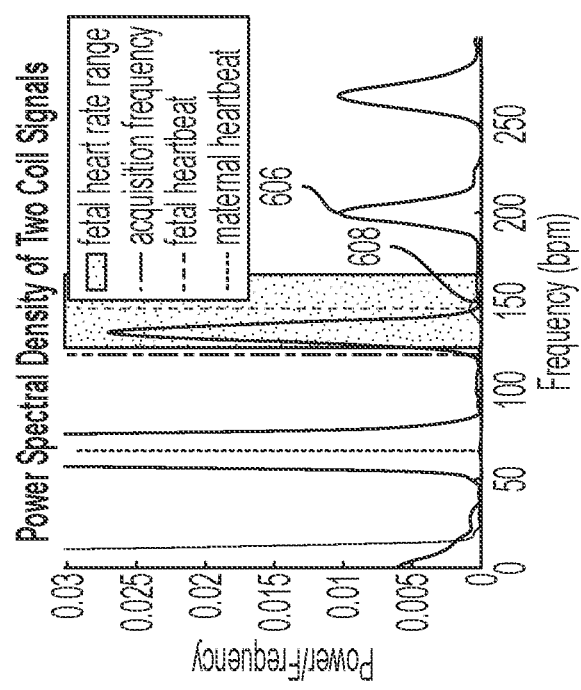
FIG. 6C is an example of calculated power spectral densities of MR signals of FIG. 6A from the center point of k-space recorded by radio frequency coils near the parental and fetal heart.

The power spectral density that is calculated from the center-of-k-space signals measured from these two radio frequency coils near the parental and fetal hearts are shown in FIG. 6C. The parental power spectral density 606 of the k-space center point signals measured from the radio frequency coil near the parental heart illustrates peaks at the parental cardiac cycle (66 bpm) and its harmonic frequencies. The second harmonic frequency exhibits a peak at twice the parental cardiac cycle (133 bpm). The fetal power spectral density 608 of the k-space center point signals measured from the radio frequency coil near the fetal heart shows a peak at the fetal heart rate (146 bpm). As shown, the second harmonic of the parental heart rate falls within the range of the fetal heart rate that is derived from the power spectral density of the center points of k-space measured from the coil near the fetal heart rate.

FIG. 6D is an example of an MR image generated from MR signals recorded by a radio frequency coil near the fetal heart, in short-axis view. The inset shows a zoomed-in view of the fetal heart.

Figure 7B:
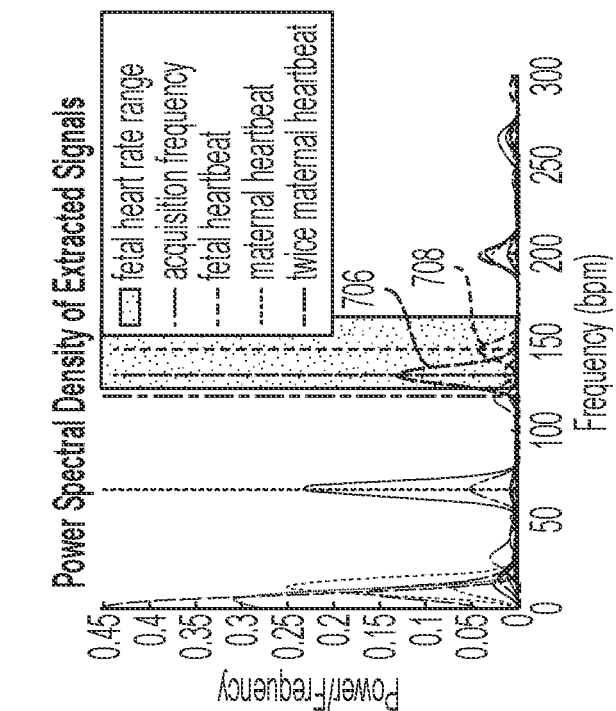
FIG. 7B is an example of calculated power spectral densities of the extracted motion signals of FIG. 7A.
Figure 7A:
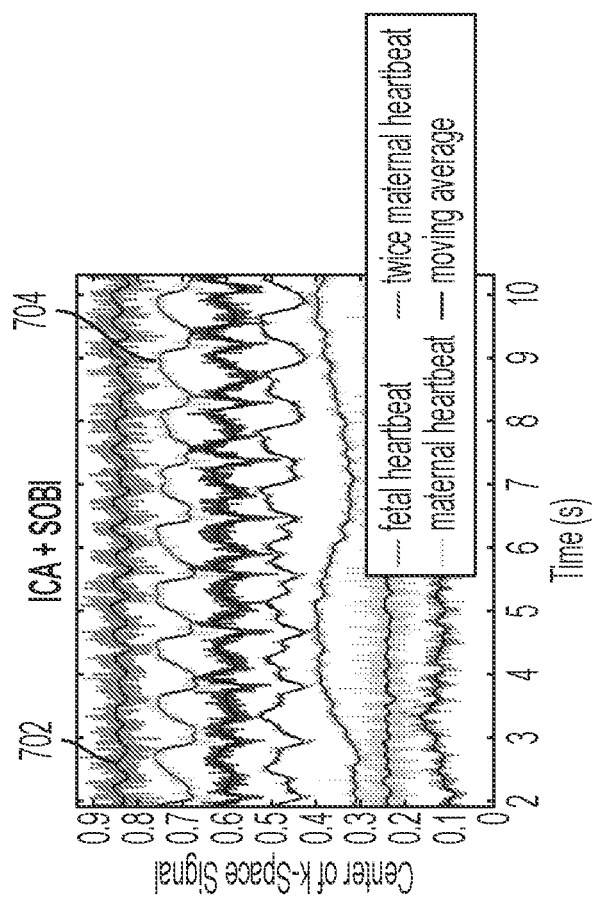
FIG. 7A is an example of motion signal components extracted from MR data obtained by imaging the fetus within a uterus of a parent using an MRI system.

To automatically detect the fetal heart rate from all the radio frequency coils, the second order blind identification (SOBI) method or independent component analysis (ICA) may be used. The SOBI method separates out different underlying source signals (i.e., motions) from the preprocessed center-of-k-space signals measured from all the radio frequency coils during MRI. These source signals may include fetal cardiac motion, the parental cardiac motion and its different harmonic frequencies, and additional sources of noise (e.g., from the MRI itself). FIG. 7A is an example of seven motion signal components extracted from MR data obtained by imaging a fetus within a uterus of a parent using an MRI system after the application of the SOBI method, including the fetal heartbeat signal 702 and the material heartbeat signal 704.

Because cardiac motion information represented in MR data from the center of k-space can have a variety of shapes, analysis of the motion may be challenging. The inventors have recognized and appreciated that the extraction of a cardiac motion signal from the center point of k-space measured from multi-array radio frequency coils may be performed using blind source separation (BSS). In BSS, a set of unobservable source signals $s(t)=[s_1(t), s_2(t), \ldots, s_{N_s}(t)]^T$ may be recovered from a set of observed mixtures $x(t)=[x_1(t), x_2(t), \ldots, x_{N_x}(t)]^T$ of the sources. The relationship between the sources, s, and the observations, x, may be given by a mixing matrix A, such that $x(t)=As(t)$, assuming a linear mixture model. The number of observations, $N_x$, may be larger than the number of sources $N_s$. In order to retrieve the sources from the measured data, it can be beneficial for the observation channels to be linearly independent. The MR data from the center of k-space may include linearly independent observation channels, since the MR data originates from different radio frequency coils positioned in different locations.

The goal of BSS is to approximate the inverse of the mixing matrix, such that the sources can be easily determined as: $s(t)=A^{-1}x(t)$. There are several approaches based on different assumptions to perform the BSS analysis. Principal component analysis (PCA, often used as a preprocessing step called pre-whitening) is a method useful for self-gating techniques for MRI. It enforces that the separated sources are mutually uncorrelated, i.e. $E[s(t)s^T(t)]=I$, where E is the expected value and I the identity matrix. Independent component analysis (ICA) extends this to the assumption of full statistical independence of the sources in higher order statistics (i.e., $f(s)=\Pi_{i=1}^{N_s}f(s_i)$, where f(s) is the probability density function of the random process s and achieves this by maximizing the non-Gaussianity of the sources.)

PCA and ICA only exploit the spatial correlations between different measurements. The signal source representing cardiac motion may be known to possess periodicity correlated with the heart rate. This temporal correlation can be exploited with the second order blind identification (SOBI) method. SOBI also enables the extraction of multiple Gaussian sources which is not possible with ICA. The assumption made in SOBI is that different sources remain uncorrelated at different time lags, but the same source is highly correlated over time. It thus assumes that the covariance matrix has the following form: $E[s(t+\tau)s^T(t)]=D$, where i is a time lag and D is a diagonal matrix. SOBI aims at the joint diagonalization of the covariance matrix at different time lags. For this application, the maximum time lag may be chosen to be the duration of 5 maximum possible heartbeats ($\approx$2.4 seconds).

The temporal correlation of the sources can also be exploited by ICA. The temporal correlation manifests itself if the signals are transformed into the frequency domain. The signals may be transformed into the frequency domain, undergo ICA, and then may be transformed them back to the time domain.

Once the different motion signals are separated using BSS, the most likely motion representing the fetal cardiac cycle may be identified. To identify the fetal heart rate, the fetal heart rate may be measured before the MRI scan to provide $f_{measured}$ using, for example, ultrasound. After the MRI scan, the power spectral density of each motion signal may be calculated using Welch's averaged periodogram and the two motion signals that contain the highest power peaks within the range of the fetal cardiac cycle (e.g., between $f_{min}=f_{measured}-15$ bpm and $f_{max}=f_{measured}+15$ bpm) may be chosen as potential fetal heartbeat signals, as shown in the example of FIG. 7B. FIG. 7B is an example of calculated power spectral densities of the extracted motion signals from the MR data of FIG. 7A. A range about the measured fetal heart rate, $f_{measured}$, is shown shaded, and two peaks are identified within the range. The two peaks correspond to twice the parental heart rate (132 bpm) and the fetal heart rate (146 bpm) as extracted from the parental heartbeat power spectral density 706 and the fetal heartbeat power spectral density 708, respectively.

The corresponding frequencies at the two peaks may be assumed to represent potential average fetal heart rates, $f_{ave}$. Two cardiac motions are selected since the motion corresponding to twice the parental heart rate cannot be easily distinguished from the fetal heartbeat. Two fetal cardiac MR images may then be reconstructed for each potential heart rate, and the sharpest image may be chosen as representing the MR image reconstructed from the most likely actual fetal heart rate.

In some embodiments, the detected cardiac motion source signal may be bandpass filtered around the detected average cardiac cycle $f_{ave}$ using a 6-order Butterworth bandpass filter. Filter distortions may be minimized by padding the signal with a thousand copies of the values at the signal borders. The cutoff frequencies for the bandpass filter may be chosen as $f_{min}^{cutoff}=\alpha \cdot f_{ave}+(1-\alpha) \cdot f_{min}$ and $f_{max}^{cutoff}=\min(\alpha \cdot f_{ave}+(1-\alpha) \cdot f_{max})$. The parameter a that determines the strength of the filter may be initially set to 0.5 and may be iteratively increased.

A moving-average-crossing algorithm (MAC) may be used to detect the cardiac cycles from the detected fetal cardiac motion signal. Firstly, the computing system may compute a moving average of the bandpass-filtered cardiac motion. The moving average and the filtered cardiac motions may then be overlaid, and the intersections between the two may be marked as "up" and "down" intercepts. Peaks and valleys of the filtered cardiac motion may be identified by determining the maxima and minima between these intersections. Cardiac cycles may then be determined for all four potential triggers (e.g., the up intercept, down intercept, peak, and valley) and the trigger that leads to the least heart rate variability is chosen as the self-gated fetal heart rate. The maximum and minimum cardiac frequencies detected by MAC may be calculated and if they differ by more than 10 bpm, the steps in D and E may be repeated with an increased filter strength (i.e. $\alpha_{new}=\alpha+0.1$). The detected cardiac cycles may then be used for grouping the 2D cine SSFP k-space data into 30 cardiac phases and reconstructing the cine MR images.

To assess the efficacy of this technique, 13 healthy pregnant volunteers (ranging from 23 to 37 years of age and gestational weeks 25-30) with informed consent underwent fetal cardiac MRI exams. All exams were performed in accordance with the guidelines set by the local research ethics committee. The Boston Children's Hospital Committee on Clinical Investigation also approved the studies, and written informed consent was obtained from all subjects. Before performing the cardiac MRI exams, one expert clinician measured the fetal heart rate (i.e., $f_{measured}$) using an ultrasound device. The scan was then performed with retrospective cardiac gating using a simulated ECG signal with a heart rate lower ($\approx$20 bpm) than the measured fetal heart rate $f_{measured}$ to ensure the imaging of the entire cardiac cycle. Then, a full stack of short-axis cine images (5-10 slices) and four chamber images (1-4 slices) was acquired from each volunteer. If scan time permitted, additional cine images in the 2-chamber left ventricle (LV) view (3 volunteers) and the left ventricular outflow track (LVOT) view (1 volunteer) were also acquired. All the scans were acquired under parental breath-hold if possible (5/7 subjects). In cases of strong fetal bulk motion, the cine images were reacquired.

All cardiac MRI exams were performed on a 1.5 T Achieva dStream scanner (Philips Healthcare, Best, the Netherlands). The imaging parameters for the cardiac self-gated 2D cine SSFP acquisition were as follows: number of measured center points for self-gating 50-200, field-of-view≈260×260 mm, in-plane resolution≈1.80×1.85 mm reconstructed to ≈0.8×0.8 mm, slice thickness 4 mm, slice gap 0.5 mm, flip angle 60°, echo time≈2.4 ms, repetition time≈3.8 ms, bandwidth 1.6 kHz, heart phases 20 interpolated to 30, SENSE factor 1, and a simulated ECG signal with a constant heart rate that overestimated the measured fetal cardiac cycle length by ultrasound. The cardiac cycles detected with the self-gating algorithm were then used to bin the data and reconstruct the final cine images.

Figure 8:
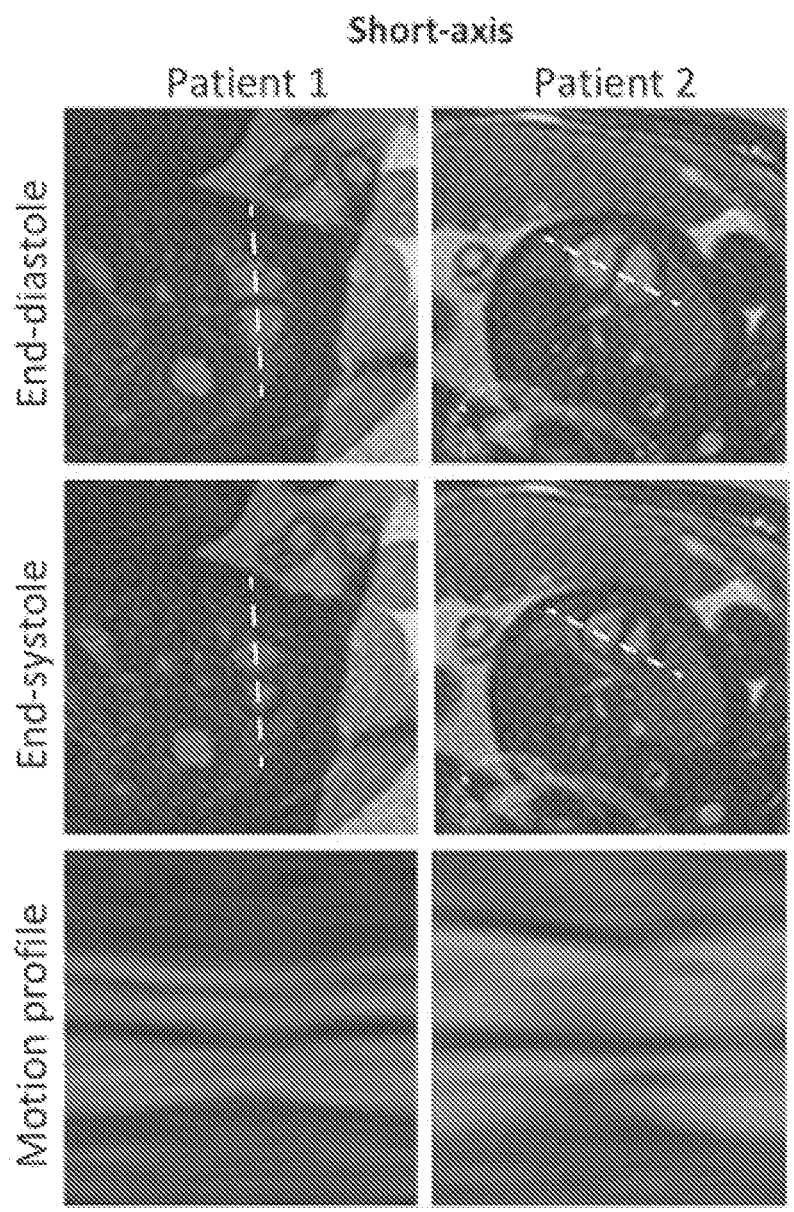
FIG. 8 is a series of short-axis MR images of two pregnant volunteers acquired using the systems and methods described herein.

The fetal cardiac self-gating MRI method described herein was successfully used to reconstruct full stacks of cine images in short-axis and 4 chamber view for 7 pregnant volunteers. FIG. 8 shows an example of reconstructed short-axis images of a mid-ventricular slice in end-systole and end-diastole from two pregnant volunteers of gestational age 27 weeks (left) and gestational age 28 weeks (right). Images are shown at end-diastole (top row), end-systole (middle row), and as a motion profile over the full cardiac cycle (bottom row). The motion profile along the dashed-white line perpendicular to the left ventricle endocardial border versus time (e.g., M-mode equivalent) is also shown for these two patients.

Figure 9:
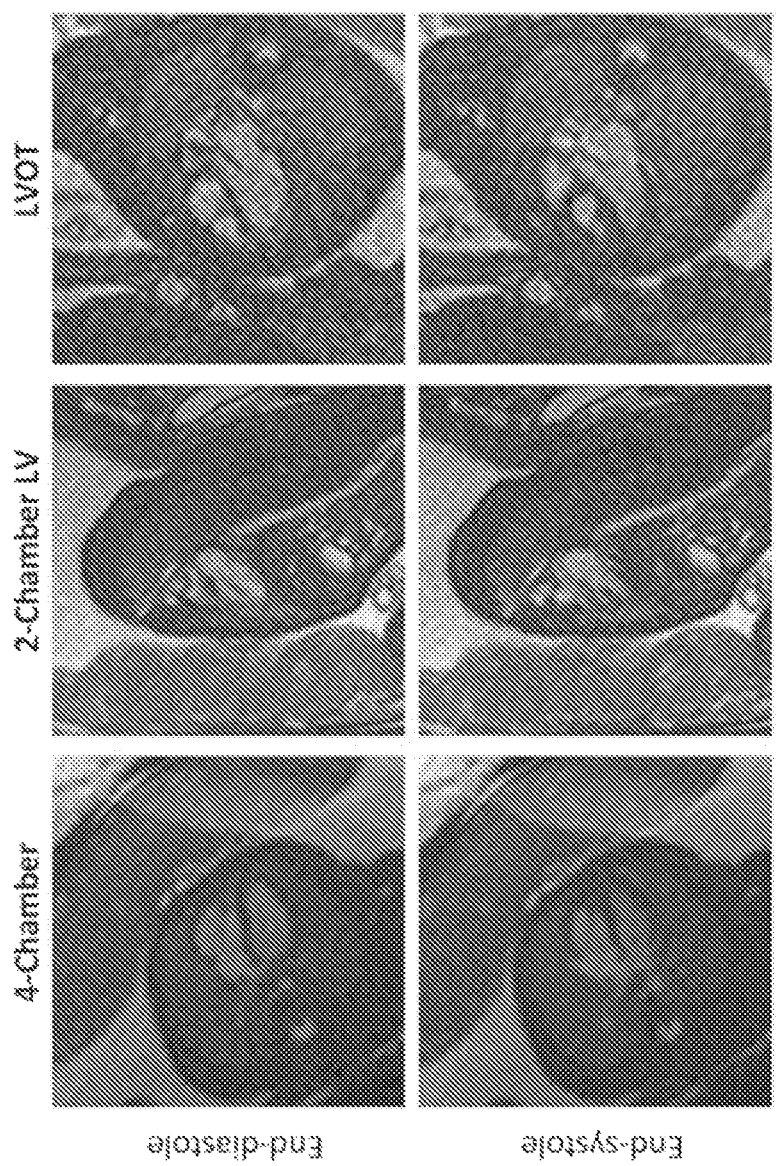
FIG. 9 is a series of MR images in 4-chamber, 2-chamber left ventricular, and left ventricular outflow track (LVOT) views acquired for three pregnant volunteers using the systems and methods described herein.

FIG. 9 is a series of MR images in 4-chamber, 2-chamber left ventricular, and left ventricular outflow track (LVOT) views acquired for three pregnant volunteers using the systems and methods described herein. The pregnant volunteers were in gestational ages of 27 weeks (left and middle columns) and 30 weeks (right column).

In this study, a novel cardiac self-gating 2D cine SSFP pulse sequence for fetal cardiac MRI was developed and tested on 13 pregnant volunteers. The self-gating algorithm produced high-quality cine images for the short-axis, 4-chamber, 2-chamber, and left ventricular outflow track views. While the self-gating fetal heart signal was very weak due to the small size of the fetal heart and measurement noise, the averaging of multiple points from the center of k-space and the use of a suitable blind source separation method enable the extraction of a reliable fetal self-gating signal. For the detection of the fetal heartbeat, the SOBI and ICA methods performed well to separate the fetal cardiac motion from parental cardiac motion and noise. SOBI works well compared to some other BSS methods because it takes advantage of both spatial and temporal information in the center of k-space.

The self-gating signal generated from the fetal heart may be observed to be very weak due to the small size of the heart, strong parental cardiac motion, and additional measurement noise (e.g., from the MRI itself). To reduce the sources of noise, it may be useful to accurately measure the center of k-space multiple times. The center-of-k-space signal may be improved if multiple points (e.g., greater than 50, between 50 and 200, or up to 200 points) from the center of k-space are acquired and averaged at each TR. A radial k-space trajectory might not be as effective as a Cartesian trajectory in reading the center of k-space, as gradient delays may not permit the radial spokes to traverse the center of k-space. The measured signal from the center of k-space can be made stronger by using a higher strength magnetic field or by increasing the number of receiver coils, in some embodiments.

The methods described herein use a Cartesian k-space trajectory that makes fast image reconstruction possible and allows for the application of existing parallel imaging techniques. These features facilitate implementation of the techniques described herein in the clinical environment. Furthermore, the techniques described herein processes the self-gating signal very quickly (e.g., within a few seconds per volumetric slice) for fetal heartbeat detection and avoids long reconstruction times that may be present in other image-based gating methods (e.g., up to two hours per slice). Unlike the DUS technique, the techniques described herein do not use an ultrasound device in situ, which eliminates the need to reposition the ultrasound device and decreases the examination time, especially for a parent at a younger gestational age when fetuses are more active.

Techniques operating according to the principles described herein may be implemented in any suitable manner. Included in the discussion above are a series of flow charts showing the steps and acts of various processes that analyze fetal cardiac MR data to derive information indicative of fetal cardiac signals and/or generate fetal cardiac MR images. The processing and decision blocks of the flow charts above represent steps and acts that may be included in algorithms that carry out these various processes. Algorithms derived from these processes may be implemented as software integrated with and directing the operation of one or more single- or multi-purpose processors, may be implemented as functionally-equivalent circuits such as a Digital Signal Processing (DSP) circuit or an Application-Specific Integrated Circuit (ASIC), or may be implemented in any other suitable manner. It should be appreciated that the flow charts included herein do not depict the syntax or operation of any particular circuit or of any particular programming language or type of programming language. Rather, the flow charts illustrate the functional information one skilled in the art may use to fabricate circuits or to implement computer software algorithms to perform the processing of a particular apparatus carrying out the types of techniques described herein. It should also be appreciated that, unless otherwise indicated herein, the particular sequence of steps and/or acts described in each flow chart is merely illustrative of the algorithms that may be implemented and can be varied in implementations and embodiments of the principles described herein.

Accordingly, in some embodiments, the techniques described herein may be embodied in computer-executable instructions implemented as software, including as application software, system software, firmware, middleware, embedded code, or any other suitable type of computer code. Such computer-executable instructions may be written using any of a number of suitable programming languages and/or programming or scripting tools, and also may be compiled as executable machine language code or intermediate code that is executed on a framework or virtual machine.

When techniques described herein are embodied as computer-executable instructions, these computer-executable instructions may be implemented in any suitable manner, including as a number of functional facilities, each providing one or more operations to complete execution of algorithms operating according to these techniques. A "functional facility," however instantiated, is a structural component of a computer system that, when integrated with and executed by one or more computers, causes the one or more computers to perform a specific operational role. A functional facility may be a portion of or an entire software element. For example, a functional facility may be implemented as a function of a process, or as a discrete process, or as any other suitable unit of processing. If techniques described herein are implemented as multiple functional facilities, each functional facility may be implemented in its own way; all need not be implemented the same way. Additionally, these functional facilities may be executed in parallel and/or serially, as appropriate, and may pass information between one another using a shared memory on the computer(s) on which they are executing, using a message passing protocol, or in any other suitable way.

Generally, functional facilities include routines, programs, objects, components, data structures, etc. that perform particular tasks or implement particular abstract data types. Typically, the functionality of the functional facilities may be combined or distributed as desired in the systems in which they operate. In some implementations, one or more functional facilities carrying out techniques herein may together form a complete software package. These functional facilities may, in alternative embodiments, be adapted to interact with other, unrelated functional facilities and/or processes, to implement a software program application, for example as a software program application such as a fetal cardiac analysis facility.

Some exemplary functional facilities have been described herein for carrying out one or more tasks. It should be appreciated, though, that the functional facilities and division of tasks described is merely illustrative of the type of functional facilities that may implement the exemplary techniques described herein, and that embodiments are not limited to being implemented in any specific number, division, or type of functional facilities. In some implementations, all functionality may be implemented in a single functional facility. It should also be appreciated that, in some implementations, some of the functional facilities described herein may be implemented together with or separately from others (i.e., as a single unit or separate units), or some of these functional facilities may not be implemented.

Computer-executable instructions implementing the techniques described herein (when implemented as one or more functional facilities or in any other manner) may, in some embodiments, be encoded on one or more computer-readable media to provide functionality to the media. Computer-readable media include magnetic media such as a hard disk drive, optical media such as a Compact Disk (CD) or a Digital Versatile Disk (DVD), a persistent or non-persistent solid-state memory (e.g., Flash memory, Magnetic RAM, etc.), or any other suitable storage media. Such a computer-readable medium may be implemented in any suitable manner, including as computer-readable storage media 1006 of FIG. 10 described below (i.e., as a portion of a computing device 1000) or as a stand-alone, separate storage medium. As used herein, "computer-readable media" (also called "computer-readable storage media") refers to tangible storage media. Tangible storage media are non-transitory and have at least one physical, structural component. In a "computer-readable medium," as used herein, at least one physical, structural component has at least one physical property that may be altered in some way during a process of creating the medium with embedded information, a process of recording information thereon, or any other process of encoding the medium with information. For example, a magnetization state of a portion of a physical structure of a computer-readable medium may be altered during a recording process.

Figure 10:
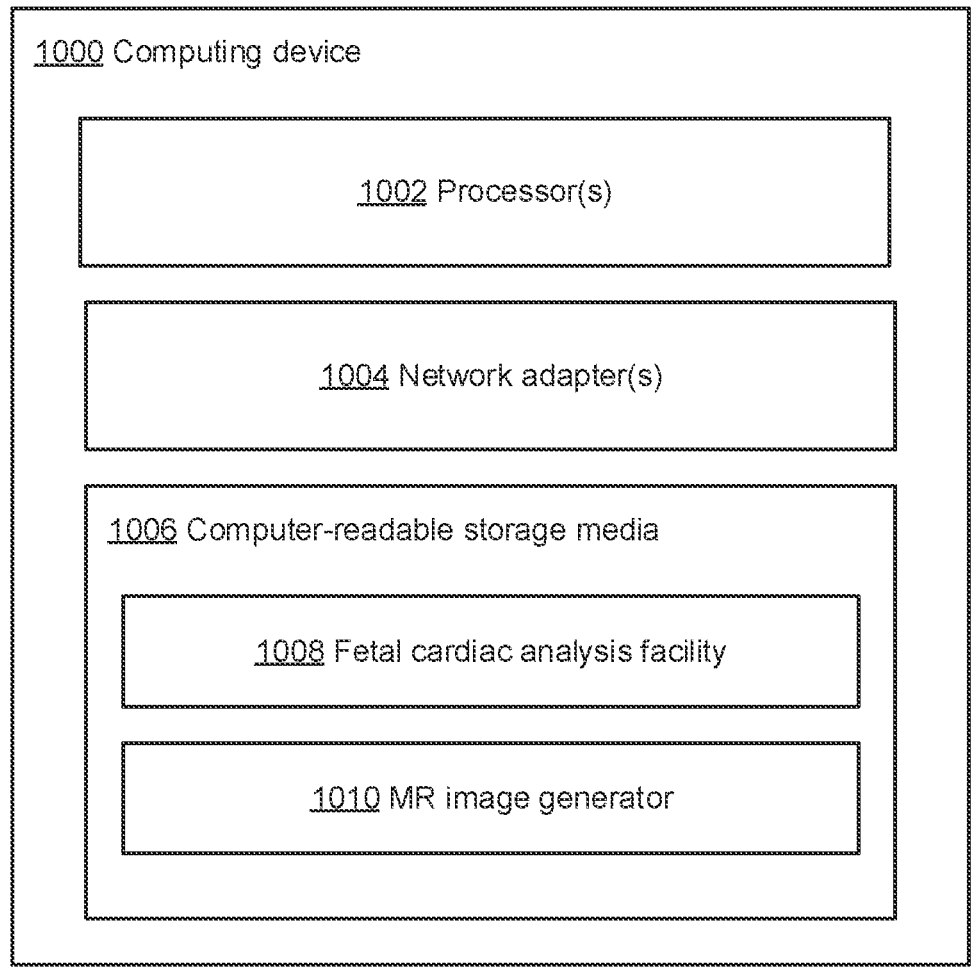
FIG. 10 is a schematic diagram of an illustrative computing device with which aspects described herein may be implemented.

In some, but not all, implementations in which the techniques may be embodied as computer-executable instructions, these instructions may be executed on one or more suitable computing device(s) operating in any suitable computer system, including the exemplary computer system of FIG. 10, or one or more computing devices (or one or more processors of one or more computing devices) may be programmed to execute the computer-executable instructions. A computing device or processor may be programmed to execute instructions when the instructions are stored in a manner accessible to the computing device or processor, such as in a data store (e.g., an on-chip cache or instruction register, a computer-readable storage medium accessible via a bus, a computer-readable storage medium accessible via one or more networks and accessible by the device/processor, etc.). Functional facilities comprising these computer-executable instructions may be integrated with and direct the operation of a single multi-purpose programmable digital computing device, a coordinated system of two or more multi-purpose computing device sharing processing power and jointly carrying out the techniques described herein, a single computing device or coordinated system of computing devices (co-located or geographically distributed) dedicated to executing the techniques described herein, one or more Field-Programmable Gate Arrays (FPGAs) for carrying out the techniques described herein, or any other suitable system.

FIG. 10 illustrates one exemplary implementation of a computing device in the form of a computing device 1000 that may be used in a system implementing techniques described herein, although others are possible. It should be appreciated that FIG. 10 is intended neither to be a depiction of necessary components for a computing device to operate as a fetal cardiac MR analysis device and/or fetal cardiac MR image generator in accordance with the principles described herein, nor a comprehensive depiction.

Computing device 1000 may comprise at least one processor 1002, a network adapter 1004, and computer-readable storage media 1006. Computing device 1000 may be, for example, a desktop or laptop personal computer, a personal digital assistant (PDA), a smart mobile phone, or any other suitable computing device. Network adapter 1004 may be any suitable hardware and/or software to enable the computing device 1000 to communicate wired and/or wirelessly with any other suitable computing device over any suitable computing network. The computing network may include wireless access points, switches, routers, gateways, and/or other networking equipment as well as any suitable wired and/or wireless communication medium or media for exchanging data between two or more computers, including the Internet. Computer-readable media 1006 may be adapted to store data to be processed and/or instructions to be executed by processor 1002. Processor 1002 enables processing of data and execution of instructions. The data and instructions may be stored on the computer-readable storage media 1006.

The data and instructions stored on computer-readable storage media 1006 may comprise computer-executable instructions implementing techniques which operate according to the principles described herein. In the example of FIG. 10, computer-readable storage media 1006 stores computer-executable instructions implementing various facilities and storing various information as described above. Computer-readable storage media 1006 may store fetal cardiac analysis facility 1008 configured to derive information indicative of fetal cardiac cycles from MR data and/or MR image generator 1010 configured to generate MR images based on MR data of a fetal heart and/or information indicative of fetal cardiac cycles of said fetal heart.

While not illustrated in FIG. 10, a computing device may additionally have one or more components and peripherals, including input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

The word "exemplary" is used herein to mean serving as an example, instance, or illustration. Any embodiment, implementation, process, feature, etc. described herein as exemplary should therefore be understood to be an illustrative example and should not be understood to be a preferred or advantageous example unless otherwise indicated.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the principles described herein. Accordingly, the foregoing description and drawings are by way of example only.

What is claimed is:

1. A method of generating a fetal cardiac magnetic resonance (MR) image of a living fetus, within a uterus of a parent of the fetus, by imaging the fetus within the uterus using a magnetic resonance imaging (MRI) system, the method comprising:
   deriving information indicative of cardiac cycles of a heart of the fetus from MR data for the fetus within the uterus, the MR data comprising MR data from a heart of the fetus and from a center of k-space, the MR data being based on data acquired in an imaging of at least the heart of the fetus within the uterus using the MRI system;
   using blind source separation to extract a parental cardiac motion signal from the MR data, the parental cardiac motion signal comprising information indicative of motion of a heart of the parent; and
   generating the fetal cardiac MR image based on the information indicative of the cardiac cycles of the heart of the fetus that was derived from the MR data.

2. The method of claim 1, wherein deriving information indicative of a cardiac cycle of the heart of the fetus comprises using blind source separation to extract one or more fetal cardiac motion signals from the MR data.

3. The method of claim 2, wherein using blind source separation to extract the one or more fetal cardiac motion signals from the MR data comprises using independent component analysis (ICA) in a frequency domain to extract the one or more fetal cardiac motion signals from the MR data.

4. The method of claim 2, wherein deriving information indicative of the cardiac cycles of the heart of the fetus further comprises determining a fetal heart rate by calculating a power spectral density of one of the one or more fetal cardiac motion signals.

5. The method of claim 4, further comprising obtaining an initial measurement of the fetal heart rate prior to acquiring the MR data, wherein deriving information indicative of the cardiac cycles of the heart of the fetus further comprises identifying local maxima within a subset of the calculated power spectral density, the subset being centered around the initial measurement of the fetal heart rate.

6. The method of claim 1, wherein imaging at least the heart of the fetus within the uterus using the MRI system comprises sampling a center point of k-space a plurality of times within a repetition period (TR) of a pulse sequence used for said imaging.

7. The method of claim 6, wherein deriving information indicative of a cardiac cycle of the heart of the fetus comprises averaging the plurality of samples of the center point of k-space.

8. The method of claim 1, wherein generating the fetal cardiac MR image comprises: grouping MR data instances of the MR data into a plurality of cardiac phases based on the derived information indicative of the cardiac cycles of the heart of the fetus; selecting a cardiac phase of the plurality of cardiac phases; and generating the fetal cardiac MR image based on the grouped MR data instances of the selected cardiac phase.

9. A method of generating a fetal cardiac magnetic resonance (MR) image of a living fetus, within a uterus of a parent of the fetus, by imaging the fetus within the uterus using a magnetic resonance imaging (MRI) system, the method comprising: deriving, from MR data comprising MR data for a heart of the fetus within the uterus, first information indicative of a first potential set of cardiac cycles of the heart of the fetus and second information indicative of a second potential set of cardiac cycles of the heart of the fetus, the MR data being based on data acquired in an imaging of at least the heart of the fetus within the uterus using the MRI system, wherein one of the first information or the second information corresponds to a set of cardiac cycles of the heart of the fetus and the other of the first information or the second information corresponds to a set of cardiac cycles of the heart of the parent; and generating at least one fetal cardiac MR image based on information indicative of one potential set of cardiac cycle of the first potential set of cardiac cycles of the heart of the fetus and the second potential set of cardiac cycles of the heart of the fetus.

10. The method of claim 9, further comprising receiving an initial fetal heart rate of the heart of the fetus within the uterus, the initial fetal heart rate being determined based at least in part on data acquired in a measurement of the initial fetal heart rate using at least one device separate from the MRI system.

11. The method of claim 10, wherein deriving the first information indicative of a first potential set of cardiac cycles of the heart of the fetus and the second information indicative of a second potential set of cardiac cycles of the heart of the fetus further comprises using the received initial heart rate of the fetus within the uterus.

12. The method of claim 11, wherein deriving the first information indicative of a first potential set of cardiac cycles of the heart of the fetus and the second information indicative of a second potential set of cardiac cycles of the heart of the fetus comprises using blind source separation to extract two fetal cardiac motion signals from the MR data.

13. The method of claim 12, wherein using blind source separation to extract the two fetal cardiac motion signals from the MR data comprises using independent component analysis (ICA) and in a frequency domain to extract the two fetal cardiac motion signals from the MR data.

14. The method of claim 12, further comprising using blind source separation to extract a parental cardiac motion signal from the MR data, the parental cardiac motion signal comprising information indicative of motion of a heart of the parent.

15. The method of claim 12, further comprising calculating a respective power spectral density of each of the extracted two fetal cardiac motion signals.

16. The method of claim 15, wherein using the received initial fetal heart rate comprises identifying local maxima within the calculated respective power spectral densities within a range centered around the received initial fetal heart rate.

17. The method of claim 9, wherein the imaging at least the heart of the fetus within the uterus using the MRI system comprises sampling a center point of k-space a plurality of times within a repetition period (TR) of a pulse sequence used for said imaging.

18. The method of claim 17, wherein deriving the first information indicative of a first potential set of cardiac cycles of the heart of the fetus and the second information indicative of a second potential set of cardiac cycles of the heart of the fetus further comprises averaging each plurality of samples of the center point of k-space for each TR.

19. The method of claim 17, wherein generating the at least one fetal cardiac MR image comprises: grouping MR data instances of the MR data into a plurality of cardiac phases based on one of the first information indicative of a first potential set of cardiac cycles of the heart of the fetus and the second information indicative of a second potential set of cardiac cycles of the heart of the fetus; selecting a cardiac phase of the plurality of cardiac phases; and generating the fetal cardiac MR image based on the grouped MR data instances of the selected cardiac phase.

20. The method of claim 19, further comprising generating at least one fetal cardiac MR image based on another of the first potential set of cardiac cycles of the heart of the fetus and the second potential set of cardiac cycles of the heart of the fetus.

21. A magnetic resonance imaging (MRI) system configured to generate a fetal cardiac magnetic resonance (MR) image of a living fetus, within a uterus of a parent of the fetus, by imaging the fetus within the uterus, the MRI system comprising:
    a magnetics system configured to, when operated, produce one or more magnetic fields during MR imaging;
    at least one radio frequency coil configured to, when operated, produce one or more radio frequency pulses during MR imaging; and
    at least one processor configured to cause the MRI system to perform operations including:
        receiving information indicative of cardiac cycles of a heart of the fetus, the information indicative of the cardiac cycles of the heart of the fetus being based on MR data acquired in an imaging of at least the heart of the fetus within the uterus using the MRI system;
        using blind source separation to extract a parental cardiac motion signal from the MR data, the parental cardiac motion signal comprising information indicative of motion of a heart of the parent; and
        generating the fetal cardiac MR image based on the information indicative of the cardiac cycles of the heart of the fetus that was derived from the MR data.

22. The MRI system of claim 21, wherein generating the at least one fetal cardiac MR image comprises: grouping MR data instances of the MR data into a plurality of cardiac phases based on the received information indicative of the cardiac cycles of the heart of the fetus; selecting a cardiac phase of the plurality of cardiac phases; and generating the fetal cardiac MR image based on the grouped MR data instances of the selected cardiac phase.

23. The MRI system of claim 21, wherein generating the fetal cardiac MR image comprises:
    identifying, based on the MR data, first and second potential fetal heart rates;
    reconstructing first and second potential fetal cardiac MR images corresponding, respectively, to the first and second potential fetal heart rates; and
    selecting the first potential fetal cardiac MR image as the fetal cardiac MR image based on relative sharpness of the first and second potential fetal cardiac MR images, wherein the second potential fetal heart rate corresponding to the second potential fetal cardiac MR image is an harmonic of a heart rate of the parent.

\* \* \* \* \*